(12) United States Patent
Nazer et al.

(10) Patent No.: US 12,109,441 B2
(45) Date of Patent: *Oct. 8, 2024

(54) EXTRACORPOREAL THERAPEUTIC ULTRASOUND FOR PROMOTING VASODILATION

(71) Applicant: Vibrato Medical, Inc., Newport Beach, CA (US)

(72) Inventors: Babak Nazer, Whittier, CA (US); John For Migliazza, Belmont Shore, CA (US)

(73) Assignee: Vibrato Medical, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,450

(22) Filed: May 1, 2023

(65) Prior Publication Data

US 2023/0310904 A1    Oct. 5, 2023

Related U.S. Application Data

(63) Continuation of application No. 16/282,237, filed on Feb. 21, 2019, now Pat. No. 11,638,841, which is a continuation of application No. PCT/US2017/056800, filed on Oct. 16, 2017.

(60) Provisional application No. 62/408,783, filed on Oct. 16, 2016.

(51) Int. Cl.
*A61N 7/02* (2006.01)
*A61N 7/00* (2006.01)

(52) U.S. Cl.
CPC ............ *A61N 7/02* (2013.01); *A61N 7/00* (2013.01); *A61N 2007/0056* (2013.01); *A61N 2007/0078* (2013.01)

(58) Field of Classification Search
CPC ................... A61N 7/02; A61N 2007/0078
See application file for complete search history.

(56) References Cited

U.S. PATENT DOCUMENTS

| | | | |
|---|---|---|---|
| 5,184,605 | A | 2/1993 | Grzezykowski |
| 5,413,550 | A | 5/1995 | Castel |
| 5,601,526 | A | 2/1997 | Chapelon et al. |
| 6,325,769 | B1 | 12/2001 | Klopotek |

(Continued)

FOREIGN PATENT DOCUMENTS

| | | |
|---|---|---|
| WO | WO 2017/062673 | 4/2017 |
| WO | WO 2018/071908 | 4/2018 |
| WO | WO 2019/204639 | 10/2019 |

OTHER PUBLICATIONS

Bovee, Using Mist Ultrasound to Accelerate the Healing of Wounds and Deep Tissue Injuries: A Case-Study, 2015, UMI Dissertation Publishing, UMI No. 3701848, pp. 1-22 (Year: 2015).*

(Continued)

*Primary Examiner* — Rochelle D Turchen
(74) *Attorney, Agent, or Firm* — Knobbe, Martens, Olson & Bear, LLP

(57) ABSTRACT

Systems and methods can include wearable, non-invasive ultrasound modalities for treating a variety of medical conditions, including but not limited to peripheral vascular disease. The modality could be therapeutic ultrasound (TUS), and be configured to promote angiogenesis within a patient via stimulation of cavitation and shear stress, among other mechanisms.

26 Claims, 20 Drawing Sheets

(56) References Cited

U.S. PATENT DOCUMENTS

| | | | |
|---|---|---|---|
| 7,125,387 B2 | 10/2006 | Kawabata et al. | |
| 7,530,958 B2 | 5/2009 | Slayton et al. | |
| 7,628,764 B2 | 12/2009 | Duarte et al. | |
| 7,645,244 B2 | 1/2010 | Mason et al. | |
| 8,197,427 B2 | 6/2012 | Ward et al. | |
| 8,292,834 B2 | 10/2012 | El-Bialy et al. | |
| 8,858,440 B2 | 10/2014 | Tyler | |
| 8,870,796 B2 | 10/2014 | Hoffmann | |
| 8,892,200 B2 | 11/2014 | Wagner et al. | |
| 8,986,342 B2 | 3/2015 | Naghavi et al. | |
| 9,078,478 B2 | 7/2015 | Ross | |
| 11,638,841 B2 | 5/2023 | Nazer et al. | |
| 2003/0009153 A1 | 1/2003 | Brisken et al. | |
| 2003/0153849 A1 | 8/2003 | Huckle et al. | |
| 2006/0241522 A1* | 10/2006 | Chandraratna | A61N 7/00 601/2 |
| 2007/0016039 A1* | 1/2007 | Vortman | A61N 7/02 601/2 |
| 2007/0055179 A1 | 3/2007 | Deem et al. | |
| 2008/0097206 A1* | 4/2008 | Chomas | A61B 8/481 600/439 |
| 2008/0132790 A1 | 6/2008 | Burton | |
| 2008/0319375 A1* | 12/2008 | Hardy | B82Y 5/00 600/431 |
| 2010/0106019 A1 | 4/2010 | Friemel et al. | |
| 2011/0178407 A1 | 7/2011 | Lu et al. | |
| 2011/0245671 A1 | 10/2011 | Sato | |
| 2012/0016239 A1* | 1/2012 | Barthe | A61B 8/4272 600/439 |
| 2012/0059294 A1 | 3/2012 | Schubert et al. | |
| 2012/0109019 A1 | 5/2012 | Schneider et al. | |
| 2012/0157889 A1 | 6/2012 | Tains et al. | |
| 2012/0165668 A1 | 6/2012 | Slayton et al. | |
| 2012/0277640 A1* | 11/2012 | Lewis, Jr. | A61B 8/4281 601/2 |
| 2013/0006153 A1 | 1/2013 | Lewis, Jr. | |
| 2013/0281856 A1 | 10/2013 | Freiburger | |
| 2014/0058292 A1 | 2/2014 | Alford et al. | |
| 2014/0155788 A1* | 6/2014 | Hoelscher | A61B 8/481 601/2 |
| 2015/0174002 A1 | 6/2015 | Burbank et al. | |
| 2016/0038770 A1* | 2/2016 | Tyler | A61N 7/00 601/2 |
| 2016/0082293 A1 | 3/2016 | Asko et al. | |
| 2016/0136462 A1 | 5/2016 | Lewis et al. | |
| 2017/0224314 A1 | 8/2017 | Slayton et al. | |
| 2017/0319858 A1* | 11/2017 | Radziemski | A61N 1/37223 |
| 2018/0296859 A1 | 10/2018 | Guha et al. | |

OTHER PUBLICATIONS

Allison Ma et al. Ethnic-specific prevalence of peripheral arterial disease in the United States. American Journal of Preventative Medicine, Apr. 2007; 32(4): 328-33.
Alson et al., Pedal Arterial Imaging. Journal of Vascular and Interventional Radiology, Jan.-Feb. 1997, pp. 10-18.
American Institute of Ultrasound in Medicine Consensus Report on Potential Bioeffects of Diagnostic Ultrasound. Journal of Ultrasound Medicine 2008; 27:503-515.
Bajwa et al., Blood Oxygenation Level Dependent CMR-Derived Measures in Critical Limb Ischemia and Changes with Revascularization. Journal of the American College of Cardiology: vol. 67, No. 4, 2016 pp. 420-431.
Belcik et al., Augmentation of limb perfusion and reversal of tissue ischemia produced by ultrasound- mediated microbubble cavitation. American Heart Association, 2015, pp. 1-9.
Belcik, et al. Augmentation of Muscle Blood Flow by Ultrasound Cavitation is Mediated by ATP and Purinergic Signaling. Purinergic Mechanisms for Ultrasound Flow Augmentation, American Heart Association Journals, 2017; 135:1240-1252.
Berger et al., Overview of lower extremity peripheral artery disease. Wolters Kluwer, Jul. 2016, www.uptodate.com in 11 pages.

Bovee, Using Mist Ultrasound to Accelerate the Healing of Wounds and Deep Tissue Injuries: A Case-Study, 2015 UMI Dissertation Publishing, UMI No. 3701848, pp. 1-22, 2015.
Bradbury et al., Bypass versus Angioplasty in Severe Ischaemia of the Leg (BASIL) trial: An intention-to-treat analysis of amputation-free and overall survival in patients randomized to a bypass surgery-first or a balloon angioplasty-first revascularization strategy. Journal of Vasculary Surgery; vol. 51 No. 10S, May Supplement 2010, pp. 5S-17S.
Cassese et al. Drug-coated Balloons for Revascularization of Infrapopliteal Arteries. Journal of American College of Cardiology: Cardiovascular Interventions vol. 9, No. 10, 2016:1072-80.
Conte et al. Suggested objective performance goals and clinical trial design for evaluating catheter-based treatment of critical limb ischemia. Journal of Vascular Surgery, Sep. 2009; vol. 50, No. 6, pp. 1462-1473.e3.
Criqui, et al. Mortality over a period of 10 years in patients with peripheral arterial disease. The New England Journal of Medicine, 1992, vol. 326, No. 6, pp. 381-386.
Discussion of the Mechanical Index and Other Exposure Parameters. Journal Ultrasound Medical, Feb. 2000; 19(2): 143-168.
Dobrenz, Reducing regulatory barriers to focused ultrasound technology; Strategies for the focused ultrasound foundation, Apr. 2014 pp. 1-40.
Feb. 28, 2018, PCT Search Report for Application No. PCT/US2017/056800 Filed on Oct. 16, 2017 in 11 pages.
Focused Ultrasound Foundation, State of the Field 2016. Retrieved from the Internet http://fusfoundation.org/images/pdf/FUSF_state_of_the_field_2016.pdf in 52 pages.
Focused Ultrasound Foundation, State of the Field 2017. Retrieved from the Internet, http://fusfoundation.org/images/pdf/FUSF_state_of_the_filed_2017.pdf in 80 pages.
Fowkes et al., Comparison of global estimates of prevalence and risk factors for peripheral artery disease in 2000 and 2010: a systematic review and analysis. Lancet, Oct. 19, 2013 in 2 pages.
Gerhard-Herman, et al., 2016 AHA/ACC Guideline on the Management of Patients with Lower Extremity Peripheral Artery Disease. Journal of the American College of Cardiology, 2016, pp. 4-87.
Guide for preparing product reports for ultrasonic therapy products. U.S. Department of Health and Human Services; Public Health Services Aug. 1996 in 15 pages.
Hanawa, et al. Low-intensity pulsed ultrasound induces angiogenesis and ameliorates left ventricular dysfunction in a porcine model of chronic myocardial ischemia; Aug. 2014 pp. 1-11.
Harris et al., Epidemiology, risk factors, and natural history of peripheral artery disease. Wolters Kluwer, May 2016, www.uptodate.com in 18 pages.
Hayes, et al., Three-MHz ultrasound heats deeper into the tissues than originally theorized. Journal of Athletic Training, Sep. 2004; 39(3):230-234.
Hirsch et al., ACC/AHA 2005 Practice Guidelines for the Management of Patients with Peripheral Arterial Disease (Lower Extremity, Renal, Mesenteric and Abdominal Aortic). American Heart Association, Mar. 21, 2006; 113: e463-e654.
International Search Report and Written Opinion Dated Aug. 16, 2019 in International Patent Application Number PCT/US2019/028170.
Jaff et al., An update on methods for revascularization and expansion of the TASC lesion classification to include below-the-knee arteries: A supplement to the inter-society consensus for the management of peripheral arterial disease (TASC II): The TASC steering committee. Catheter Cardiovascular Intervention, Oct. 2015 in 2 pages.
Kannel et al., Update on some epidemiologic features of intermittent claudication: the Framingham Study. Journal of American Geriatric Society. Jan. 1985 in 2 pages.
Kibbe et al., Safety and efficacy of plasmid DNA expressing two isoforms of hepatocyte growth factor in patients with critical limb ischemia. Gene Therapy, 2016, 23, 306-312.
Kinlay, Management of Critical Limb Ischemia. American Heart Association; Circulation Cardiovascular Interventions, 2016 pp. 1-10.

(56) References Cited

OTHER PUBLICATIONS

Manzi et al., Revascularization of tibial and foot arteries: Below the knee angioplasty for limb salvage. Angioplasty, Various Techniques and Challenges in Treatment of Congenital and Acquired Vascular Stenoses, Mar. 2012; pp. 209-236.

Manzi et al., Vascular imaging of the foot: The first step toward endovascular recanalization. Vascular/Interventional Radiology October Special Issue 2011, pp. 1623-1636.

Miller et al., Overview of Therapeutic Ultrasound Applications and Safety Considerations. Journal Ultrasound Medicine, Apr. 2012; 31(4): 623-634.

Mills, Classification of lower extremity peripheral artery disease. Wolters Kluwer, Jul. 2016, www.update.com in 8 pages.

Mohler, et al. Management of claudication. Wolters Kluwer May 2016, www.uptodate.com in 16 pages.

Mohler, Investigation therapies for treating symptoms of lower extremity peripheral artery disease. Wolters Kluwer, Jul. 2016, www.uptodate.com In 11 pages.

Nazer, et al. Therapeutic Ultrasound Promotes Reperfusion and Angiogenesis in a Rat Model of Peripheral Arterial Disease. Circulation Journal, vol. 79, Sep. 2015, pp. 2043-2049.

Neschis et al., Clinical features and diagnosis of lower extremity peripheral artery disease. Wolters Kluwer, Jun. 2014, www.uptodate. com in 13 pages.

Neschis et al., Treatment of chronic lower extremity critical limb ischemia. Wolters Kluwer, Jul. 2015, www.uptodate.com in 15 pages.

Nishida et al. Extracorporeal Cardiac Shock Wave Therapy Markedly Ameliorates Ischemia-Induced Myocardial Dysfunction in Pigs in Vivo. American Heart Association, 2004, 110:3055-3061.

Norgren et al. Inter-Society consensus for the management of peripheral arterial disease (TASC II). Journal or Vascular Surgery, Jan. 2007, pp. S5A-S67A.

Pinto et al., Peripheral Arterial Disease: the growing role of endovascular management. Poster C-1931, DOI: 10.1594/ecr2012/C-1931, European Society of Radiology, 2012 in 23 pages.

Pomposelli et al., Society for vascular surgery practice guidelines for atherosclerotic occlusive disease of the lower extremities: Management of asymptomatic disease and claudication. Journal of Vascular Surgery, vol. 61, No. 3S, Mar. 2015, pp. 1S-41S.

Rosenfield et al., Trial of a paclitaxel-coated balloon for femoropopliteal artery disease. The New England Journal of Medicine, Jul. 2015, pp. 145-153.

Sanctis et al., Effects of shock waves on the microcirculation in critical limb ischemia (CLI). Angiology, The Journal of Vascular Disease, vol. 51, Aug. 2000, No. 8, Part 2 in 2 pages.

Shishegbor, et al. Critical Limb Ischemia. Journal of American College of Cardiology: 2016, vol. 68, No. 18, pp. 2003-2015.

Sumpio et al., Use of Hyperspectral Imaging to Assess Vascular Dysfunction in Arterial Disease. Journal of Vascular Surgery; Jan. 2016; vol. 63, No. 1 pp. 293-294.

Tendera et al. ESC Guideline on the diagnosis and treatment of peripheral artery diseases. European Heart Journal, 2011; 32, pp. 2851-2906.

Tsuruta et al., Therapeutic ultrasound as a potential male contraceptive: power, frequency and temperature required to deplete rat testes or meiotic cells and epididymides of sperm determined using a commercially available system. Reproductive Biology and Endocrinology, 2012, 10:7 pp. 1-15.

U.S. Department of Health and Human Services Food and Drug Administration Center for Devices and Radiological Health, Marketing Clearance of Diagnostic Ultrasound Systems and Transducers, Guidance for Industry and Food and Drug Administration Staff, Jun. 27, 2019, Rockville, MD.

Watson, T. Therapeutic Ultrasound. Electrotherapy on the Web, Retrieved from the Internet, http://www.electrotherapy.org/assets/Downloads/Therapeutic%20Ultrasound%202017.pdf (2017) in 36 pages.

Watson, T. Ultrasound Dose Calculations. Electrotherapy on the Web, Retrieved from the Internet, http://www.electrotherapy.org/assets/Downloads/Ultrasound%20Dose%20Calculations%202017.pdf (2017) in 7 pages.

\* cited by examiner

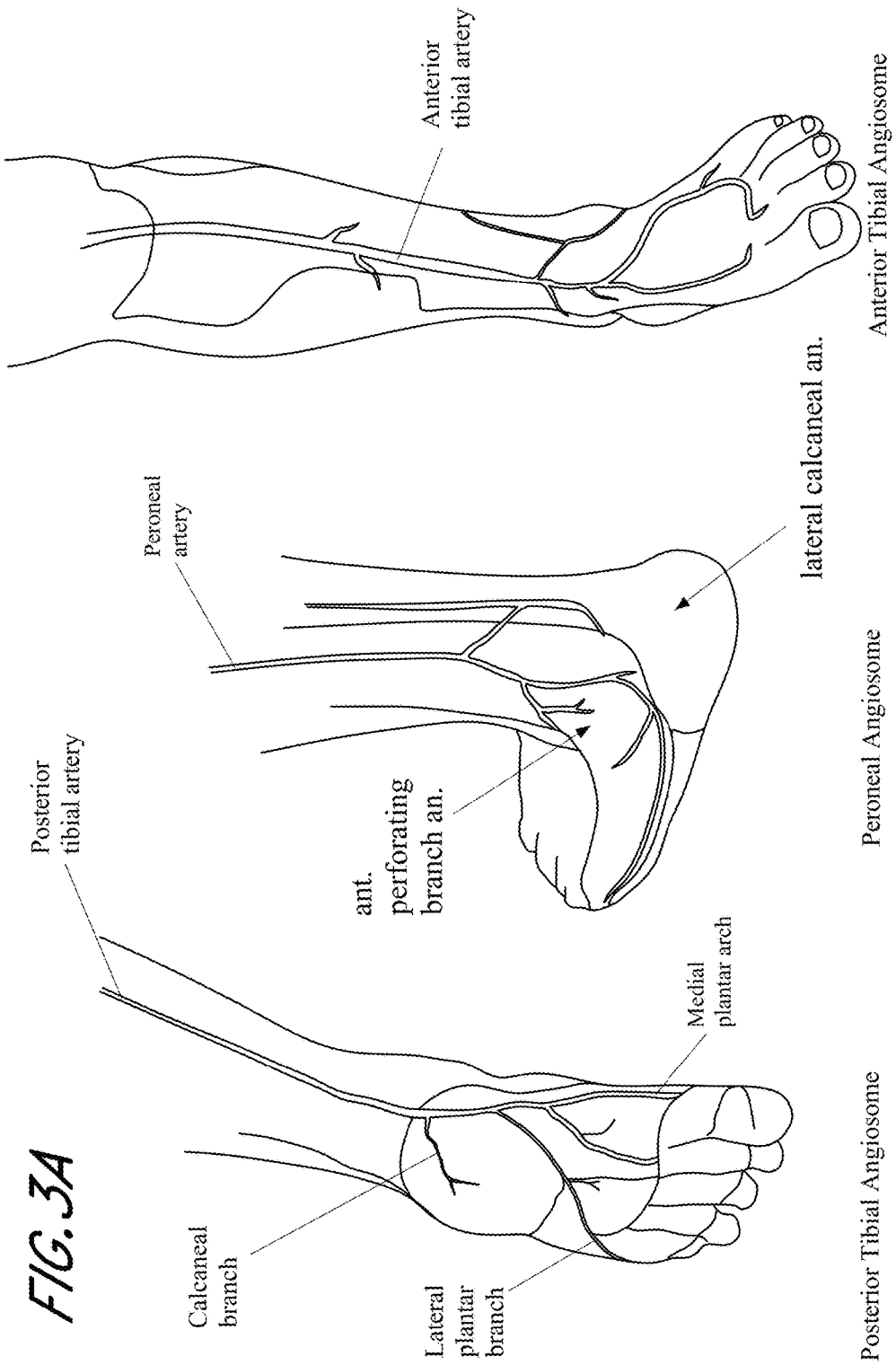

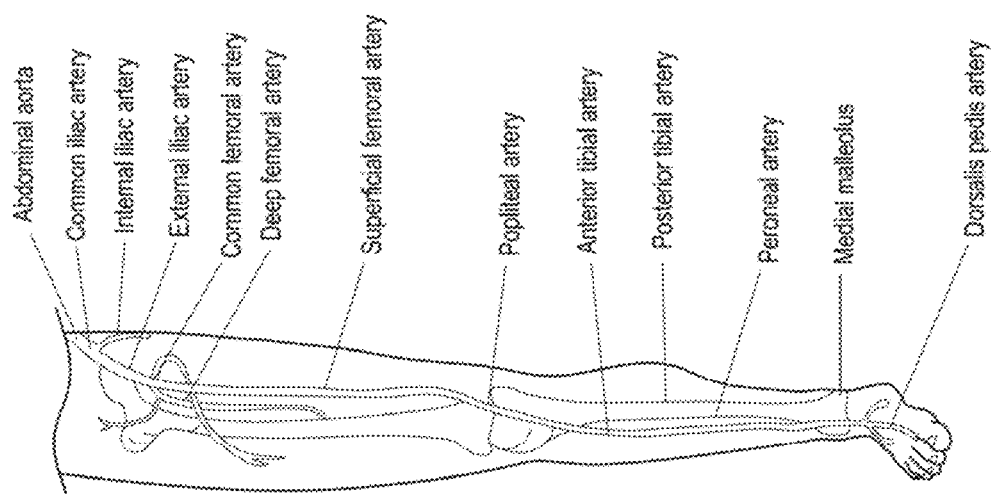
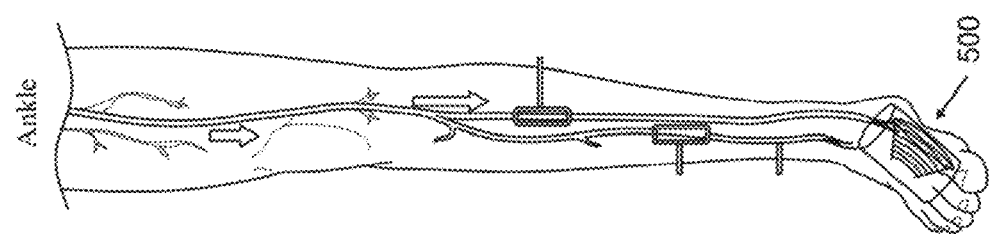
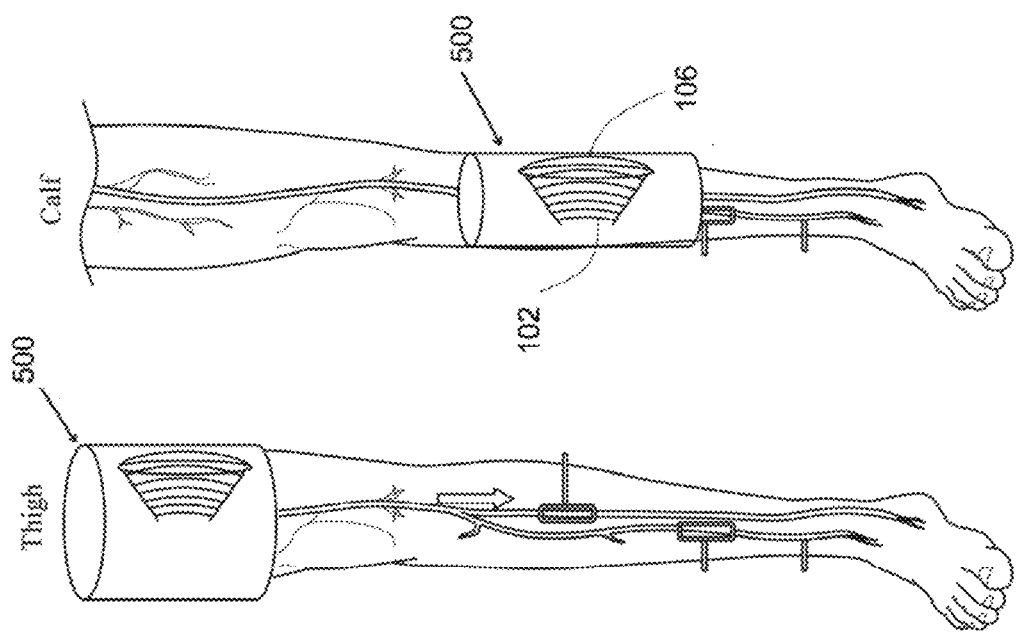
FIG. 5A   FIG. 5B   FIG. 5C   FIG. 5D

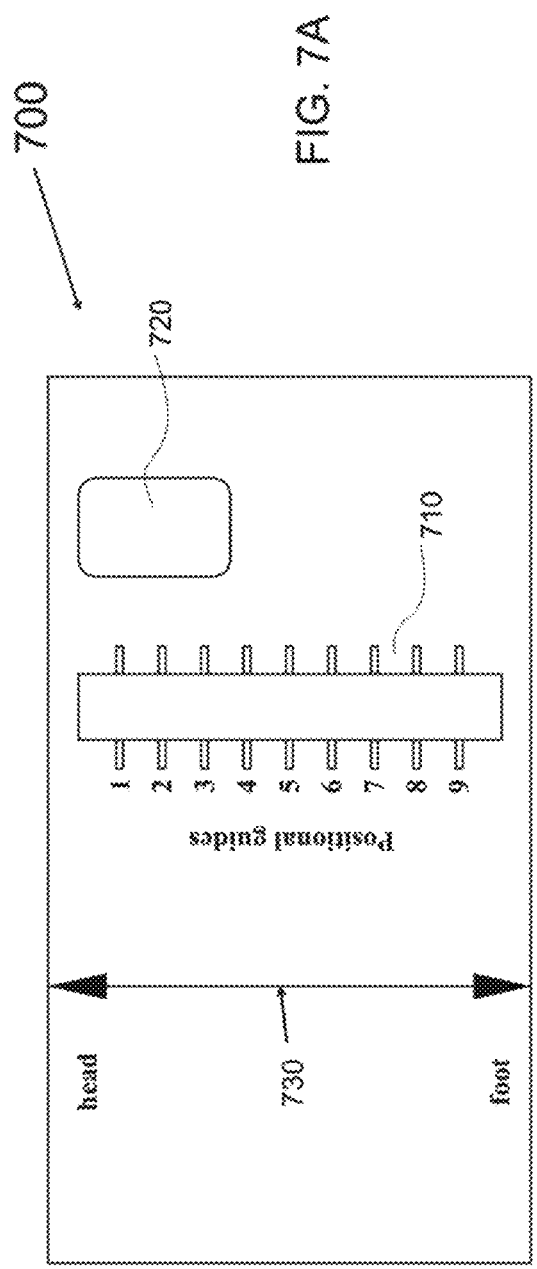
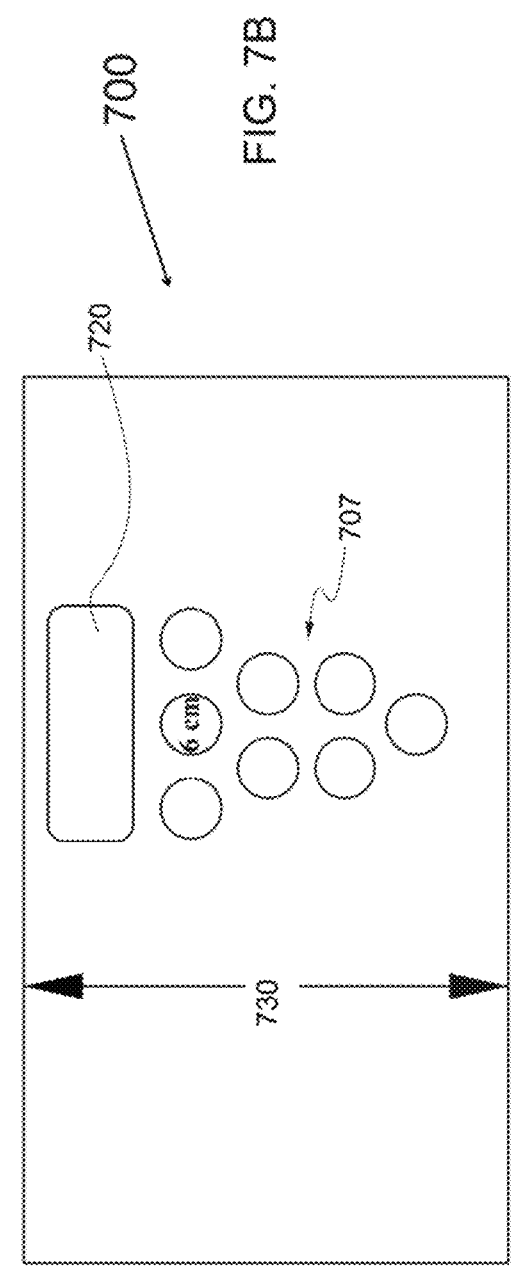

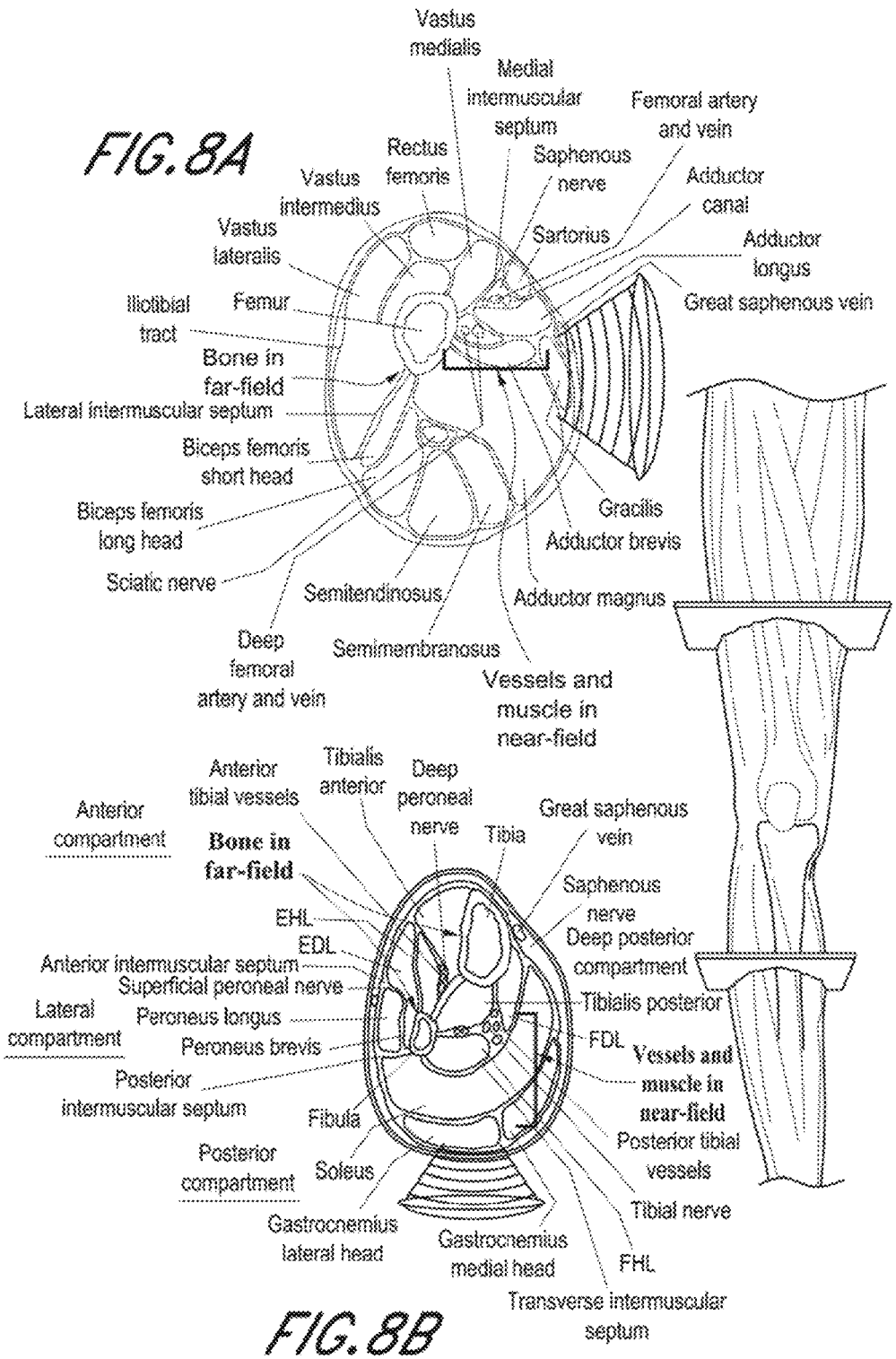

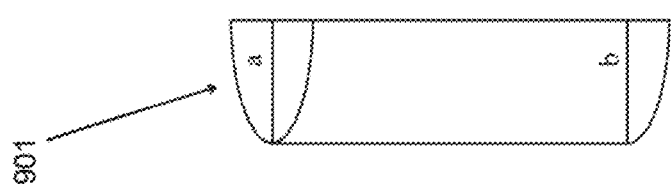
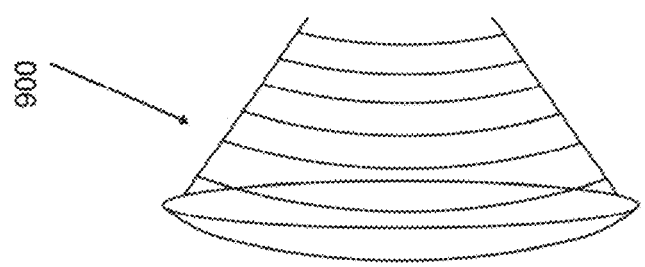
FIG. 9

| Anatomic Placement | Macro-SFA | Macro-gastroc | Macro-PTA | Macro-dorsal arch | Macro-plantar arch | Bone in near field |
|---|---|---|---|---|---|---|
| Medial thigh | | | | | | |
| Posterior calf | | | | | | |
| Anterior calf | | | | | | |
| Dorsal midfoot | | | | | | |
| Plantar midfoot | | | | | | |

Superficial Femoral Artery / Popliteal / Infrapopliteal / Pedal

FIG. 11

EXTRACORPOREAL THERAPEUTIC ULTRASOUND FOR PROMOTING VASODILATION

This application is a continuation of U.S. application Ser. No. 16/282,237, filed Feb. 21, 2019, which is a continuation of PCT Application No. PCT/US2017/056800, filed on Oct. 16, 2017, which claims the benefit under 35 U.S.C. § 119(e) as a nonprovisional application of U.S. Prov. App. No. 62/408,783 filed on Oct. 16, 2016, which is incorporated by reference in its entirety.

BACKGROUND

Peripheral arterial disease (PAD) is a highly prevalent condition, affecting approximately 202 million people worldwide and 8.5 million people in the USA. Of these, approximately one-third are symptomatic with claudication (lower extremity muscle pain with walking that limits activity), and 2-3% progress to critical limb ischemia (CLI), which is a highly morbid condition associated with resting pain, skin ulcers, and gangrene, often requiring amputation.

Current treatments for PAD have demonstrated limited efficacy. Patients with asymptomatic PAD can be treated with anti-platelet medications (e.g., aspirin, clopidogrel) and cholesterol-lowering medications such as statins in an attempt to reduce lower extremity atherosclerotic burden and to treat concomitant coronary artery disease (CAD). However, approximately 75% progress to develop symptoms of claudication or CLI. Patients with claudication have been shown to benefit from supervised exercised therapy and the medication cilostazol, however approximately 30% progress with worsening claudication, or to develop CLI. Revascularization with bypass surgery, angioplasty or stent implantation is recommended for refractory claudication or CLI, but is associated with 20-40% rates of restenosis.

Recently, acoustic energy modalities such as shock wave therapy (SWT) and therapeutic ultrasound (TUS; also referred to in prior literature as high-intensity focused ultrasound (HIFU) or low-intensity pulsed ultrasound (LIPUS)) have been shown to promote angiogenesis and improve perfusion in CAD. SWT is currently clinically approved in Europe and Japan for the treatment of refractory angina, but not PAD. The above treatments currently require intermittent treatments, such as for 20 minutes approximately three times a week with devices that require positioning and application by a healthcare provider. This potentially significantly limits clinical use as it can be time-intensive for health care providers, and also may merely provide temporary increases in blood flow via vasodilation. While approved/marketed and non-invasive TUS devices do currently exist, to the inventors' knowledge, none are designed for the human lower extremity, including the calf in some cases, and their acoustic amplitudes, frequencies, and fields are insufficient to generate the vascular bioeffects necessary for reperfusion of PAD patients. As such, more efficacious systems and methods are needed, including wearable systems that can be comfortably worn at home by patients for extended durations and provide relatively long-term clinical benefits such as increased blood flow and symptomatic relief.

SUMMARY

Systems and methods as disclosed herein can offer in some embodiments a non-invasive, non-surgical, outpatient treatment for peripheral vascular disease (PVD), including PAD and a variety of other indications, which can be used throughout the lifespan of the patient to treat symptoms and prevent disease recurrence. Some embodiments can advantageously reduce the incidence of amputations, hospitalizations and other complications of advanced PAD, adding substantial value for patients, physicians, providers, and payers alike. Some embodiments can also be used as an adjunctive treatment to invasive procedures, augmenting the capacity of the limited number of physicians trained in endovascular techniques.

Systems and methods can include wearable, non-invasive ultrasound modalities for treating a variety of medical conditions. These conditions include but are not limited to peripheral vascular disease (including PAD), and venous disease such as venous insufficiency. Conventional TUS devices used for physical therapy, CAD, and other medical indications are configured with the sole, supposed goal of promoting vasodilation and increased blood flow, although evidence for increased blood flow and the mechanisms of these effects have so far not yet been described. In contrast, in some embodiments, systems and methods as disclosed herein can advantageously promote not only vasodilation, but also unexpectedly long-term angiogenesis and collateralogenesis through one, two, or more ultrasound-mediated mechanisms. Not to be limited by theory, these mechanisms can include, for example, stimulation of angiogenesis, including collateralogenesis and/or increased microvascular density through shear stress and cavitation.

In some embodiments, disclosed herein are methods of treating peripheral vascular disease. The methods can stimulate angiogenesis and/or collaterogenesis within a patient in some cases. The methods can include providing a wearable non-invasive device. The device can include, for example, a housing material that can be flexible in some cases. The device can also include one transducer, or an array of ultrasound transducers operably attached to the housing material. The method can also include positioning the device and the transducer or array of transducers proximate a skin surface of a patient above at least one target site angiosome below the knee where angiogenesis is desired, and such that the flexible housing material and the array of ultrasound transducers substantially conforms to the skin surface of one or more of the calf, ankle, and foot of the patient, which can eliminate sharp angles present between adjacent panels of a housing, in some cases. The method can be utilized over a set period of time and number of treatment sessions to cause a therapeutically effective amount of ultrasonic energy to be directed toward the target site angiosome, thereby stimulating cavitation and shear stress within tissue at the target site angiosome, thereby promoting angiogenesis and/or collaterogenesis within the patient. In some embodiments, the ultrasonic energy can have a surface intensity:depth ratio of between about 0.10 W/cm$^3$ and about 0.60 W/cm$^3$. In some embodiments, the ultrasonic energy has a frequency of between about 0.5 MHz and about 5 MHz, between about 1 MHz and about 3 MHz, or other frequencies as disclosed elsewhere herein. The ultrasonic energy can have, for example, a peak negative pressure of between about 1 MPa and about 4 MPa. The method can also include positioning the array of transducers above at least two target site angiosomes. The target site angiosomes can include, for example, the medial calcaneal artery angiosome; the medial plantar artery angiosome; the dorsalis pedis artery angiosome; the lateral calcaneal artery angiosome, and the anterior perforating branch artery angiosome. The method can also include measuring the reflected acoustic power of the ultrasonic energy from at least one transducer of the array of transducers. The method can include discontinuing directing the ultrasonic energy from the at least one transducer found to have a reflected acoustic power above a predetermined threshold. In some embodiments, the method can include measuring blood flow in real time over the at least one angiosome, and adjusting parameters of the ultrasonic energy based on the measured blood flow. The surface area of the transducer or array of transducers can cover, for example, at least about 40%, 60%, 80%, or more of a surface area of the entire wearable device.

The modality could be, for example, therapeutic ultrasound (TUS—and may incorporate HIFU, LIPUS, and/or other pulsed or continuous wave acoustic energies), and be configured to promote angiogenesis and/or collaterogenesis within a patient. Methods can include in some embodiments stimulating angiogenesis and/or collaterogenesis within a patient, including providing a wearable non-invasive device that is not catheter-based or invasive in some cases, and comprising at least one ultrasound transducer or an array of transducers; positioning the at least one ultrasound transducer proximate a skin surface of a patient above a target site below the skin surface where angiogenesis is desired; and causing a therapeutically effective amount of ultrasonic energy over a set time period to be directed toward the target site, thereby stimulating angiogenesis within the patient. In some embodiments, the energy can be delivered with a device that is not necessarily wearable or does not have wearable components, e.g., endovascularly from one, two, or more transducers or a transducer array coupled to a catheter, with energy delivery and other parameters as described for example herein. The wearable device can be activated continuously (in pulsed form) for at least 1, 2, 4, or more hours daily, or for overnight use for example. The wearable device can be circumferentially or non-circumferentially wrapped around a portion of a body, such as an extremity of the patient. The extremity could be an upper or lower extremity, unilaterally or bilaterally. In some embodiments, the skin surface is on at least one of a thigh, a calf, an ankle, or the foot of a patient. The method can involve moving the device in a cranio-caudal direction during use, and/or rotating the device around a longitudinal axis of the device during use. Positioning the at least one ultrasound transducer proximate a skin surface can include aligning a positioning guide on a sleeve of the device anteriorly or posteriorly with respect to an extremity of the patient. The at least one ultrasound transducer or array of transducers can be positioned, for example, on the medial surface of the patient's thigh; on the posterior surface of the patient's calf; on the anterior surface of the patient's ankle; on the inferior/plantar surface of the patient's foot; on the neck proximate the carotid artery; or on the torso proximate the renal artery. Blood flow at the target site can be measured, and the ultrasonic energy increased or decreased based off the measured blood flow. The method can also include sensing the temperature at the skin surface, and decreasing or terminating the ultrasonic energy delivery if the temperature is above a pre-determined level.

In some embodiments, in some systems and methods the wearable device can be applied to the patient for treatment at least 3 days a week, or at least about 1 month. The ultrasonic energy can be delivered below the sensation threshold of the patient in some cases. The transducer or array, or the entire device could include, for example, solid piezoelectric materials and a backing material. The device can include, in some cases, a flexible surface to allow for conformal or flexible apposition to the skin surface of the patient. The method can also involve assessing for the presence of bone in a near-field via an imaging modality, and adjusting the positioning of the transducer or a parameter of the ultrasonic energy if bone is identified in the near-field. Ultrasound parameters can be adjusted such that the target site is in a near-field, and bony structures of the patient are in a far-field. Data regarding a therapy session can be recorded, and transmitting the data to a remote device in some cases. A user interface can be activated to adjust a parameter regarding the ultrasonic energy based on the comfort level of the patient. In some embodiments, the therapeutically effective amount of ultrasonic energy also stimulates vasodilation at the target site within about 24 hours of a therapy session. Systems and methods as disclosed herein can be utilized for a wide variety of indications, including the treatment or prevention of acute limb ischemia, chronic limb ischemia, diabetic foot ulcers, or restless legs syndrome. A target site can include, or be substantially limited to, for example, the gastrocnemius muscle, soleus muscle, posterior tibial artery, plantar arch arteries, or others. In some embodiments, an array of transducers can be provided that can include (or the transducer housing or backing material connecting the transducers can include), for example, circular, oval, spherical, rectangular, rhomboid, trapezoidal, or other cross-sections. In some embodiments, the method can include sensing reflected power back at the transducer or transducer array in real time, and discontinuing the therapy if the reflected power sensed is greater than a predetermined value. In some embodiments, the plurality of target sites can include one or more of the medial thigh, posterior calf, anterior calf, dorsal midfoot, and plantar midfoot. The therapeutically effective amount of ultrasonic energy can be directed to the plurality of target sites concurrently, or one, two, or more at a time. Some embodiments can include measuring perfusion at the target site in real time or substantially real time, and outputting a parameter relating to perfusion onto a display. In some aspects, a parameter of the ultrasonic energy can be adjusted after measuring perfusion at the target site. The ultrasonic energy can include, for example, a surface intensity:depth ratio of between about 0.10 $W/cm^3$ and about 0.60 $W/cm^3$.

In some embodiments, disclosed are systems for stimulating angiogenesis within a patient. The systems can include a wearable non-invasive device including an elastic sleeve. The system can also include at least one TUS transducer or array configured to be positioned proximate a skin surface of a patient above a target site below the skin surface where angiogenesis is desired. The ultrasound transducer/array can be configured to cause a therapeutically effective amount of ultrasonic energy over a set time period to be directed toward the target site, thereby stimulating cavitation and shear stress within tissue at the target site, thereby promoting angiogenesis within the patient. A portable power supply can be attached to the sleeve. In some embodiments, an adhesive gel pack can be optionally positionable between the at least one ultrasound transducer and the elastic sleeve.

In some embodiments, the at least one TUS transducer can be configured to deliver ultrasonic energy at a frequency of between about 500 kHz and about 5 MHz, or between about 1 MHz and about 3 MHz or other values as described elsewhere herein. The at least one TUS transducer can be configured to deliver ultrasonic energy at a PRF of between about 1 Hz and about 3 Hz in some cases, or other values as described elsewhere herein. The at least one TUS transducer can be configured to deliver ultrasonic energy at a pulse duration of between about 1 ms and about 10 ms, or other values as described elsewhere herein. In some embodiments, the at least one TUS transducer is configured to deliver ultrasonic energy at a duty factor of between about 0.5% and about 2%, or other values as described elsewhere herein. The at least one TUS transducer can be configured to deliver ultrasonic energy at a peak negative pressure of between about 1 MPa and about 4 MPa, or other values as described elsewhere herein. The at least one TUS transducer can be configured to deliver ultrasonic energy at a an acoustic dose of between about 250-2000 mW/cm$^2$, and a surface intensity and/or derated Isppa of between about 50-1000 W/cm$^2$.

In some embodiments, disclosed herein is a wearable system for stimulating angiogenesis within a patient. The system can include a wearable non-invasive device that can include an elastic sleeve device comprising a proximal end and a distal end. The system can also include an array of TUS transducers configured to be positioned proximate a skin surface of a patient above at least one below-the-knee target site angiosome where angiogenesis is desired. The array of ultrasound transducers can be configured to substantially conform to a calf, ankle, and/or foot of the patient. The array of ultrasound transducers can be further configured to cause a therapeutically effective amount of ultrasonic energy over a set time period to be directed toward the target site, thereby stimulating cavitation and shear stress within tissue at the target site, thereby promoting angiogenesis within the patient at the target site. The distal end of the sleeve, sock, or other wearable housing can have a closed or open distal end. The system can be configured in some cases to have any number of the following non-limiting parameters: a surface intensity:depth ratio of less than about 0.60 W/cm3; a frequency of between about 0.5 MHz and about 5 MHz or between about 1 MHz and about 3 MHz; and/or a peak negative pressure of between about 1 MPa and about 4 MPa. In some embodiments, at least some transducers of the array of transducers are directly adjacent each other, or spaced apart by no more than about 10 cm, 8 cm, 6 cm, 4 cm, 2 cm, 1 cm, 0.5 cm, 0.1 cm, or less from each other.

In some embodiments, an ultrasound imaging component may be combined into the device using the same transducer(s) that provide therapy, or separate transducers. This may use A-, M- or B-mode ultrasound imaging to assess for high acoustic reflection in the near-field which would suggest that there is bone or other more echogenic material in the near-field of the treatment area.

In some embodiments, wearable systems and methods can include any number of elements or features or combinations thereof as disclosed herein.

BRIEF DESCRIPTION OF THE DRAWINGS

FIG. 3A schematically illustrates 3 main arteries and 6 angiosomes of the below-the-knee lower extremity.

FIG. 4A demonstrates a three-component embodiment with elastic sleeve, battery/interface console, and single element transducer. FIG. 4B demonstrates an embodiment with an 8-transducer array positioned over the posterior calf. FIG. 4C demonstrates positioning of transducer array over the gastrocnemius and soleus muscles for the calf embodiment.

FIG. 4I illustrates inferior and superior views of the foot and target locations for the delivery of therapeutic energy thereto.

FIGS. 7A-7B schematically illustrates two embodiments of the wearable ultrasound sleeve displayed in unwrapped form. FIG. 7A includes an indicia of positioning, positioning guides, a transducer dock, and battery dock. FIG. 7B demonstrates an embodiment of the sleeve with an 8-transducer array, positioning line, and battery/interface.

FIGS. 8A-8D illustrates non-limiting positions of an ultrasound transducer adjacent the skin surface of an anatomical target location. In FIG. 8A, the transducer (or array) is illustrated positioned along the medial aspect of the thigh, maintaining the femoral artery in the acoustic near-field and femur in far-field so as to maximize vascular exposure and minimize bone exposure of acoustic tissue. In FIG. 8B, the transducer (or array) is positioned over the posterior aspect of the calf, maintaining the gastrocnemius, soleus, and posterior tibial artery in the near-field, and tibia and fibula in far-field. In FIG. 8C, the transducer (or array) is positioned over the plantar mid-foot, maintaining the plantar arterial arch in the near-field and metatarsals in the far-field. FIG. 8D schematically illustrate additional vessels on the dorsal and plantar surfaces of the foot.

FIG. 9 illustrates an embodiment of a single-element transducer having a circular geometry with a spherical curve, as well as a rectangular geometry with a cylindrical curve. The transducer could in some embodiments include a taper with multiple radii of curvature including first and second radii of curvatures as illustrated.

In some embodiments, each transducer could have a duty cycle that is up to 1/(total number of transducers), for example in an array of 8 transducers, each may have up to a 12.5% duty cycle. FIGS. 10A-B demonstrate two shapes of arrays of 16 circular, 4 cm diameter transducers (FIG. 10A being a trapezoidal shape, and 10B being a diamond or truncated diamond shape). FIGS. 10C-D demonstrate two shapes of arrays of 8 circular, 6 cm diameter transducers (FIG. 10C being a trapezoidal shape, and FIG. 10D being a diamond or truncated diamond shape). FIGS. 10E-F demonstrate two shapes of arrays of 4 circular, 9 cm diameter transducers (with FIG. 10E being a trapezoidal shape and FIG. 10F being a diamond or truncated diamond shape).

FIG. 11 illustrates non-limiting embodiments of a matrix of anatomic locations of transducer/array placement to optimize macrovascular collateralogenesis and microvascular angiogenesis.

DETAILED DESCRIPTION

Disclosed herein are systems and methods including wearable, non-invasive ultrasound modalities for treating a variety of medical conditions, including but not limited to PVD. The devices can be advantageously configured to achieve a variety of beneficial clinical effects, including but not limited to angiogenesis via collateralization and/or an increase in microvascular density.

SWT and TUS treatments of both CAD and PAD to date have been limited by small effect size. Effects of SWT on PAD patients were modest, and animal studies have shown only a 24% increase in pedal blood flow with TUS and 18% with SWT.

Figure 1:
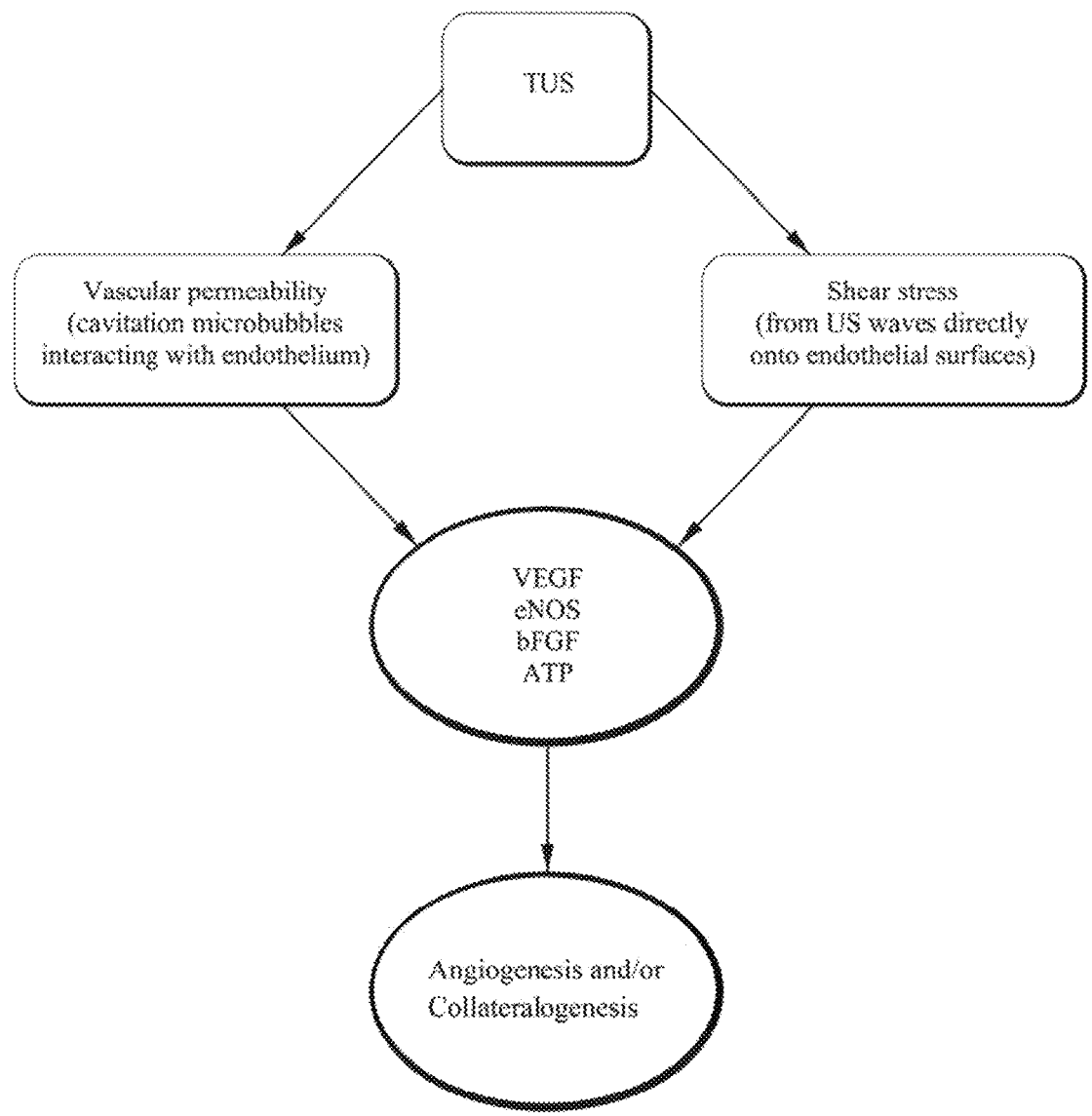
FIGS. 1 and 2 illustrates potential mechanisms of action of a TUS wearable device.
Figure 2:
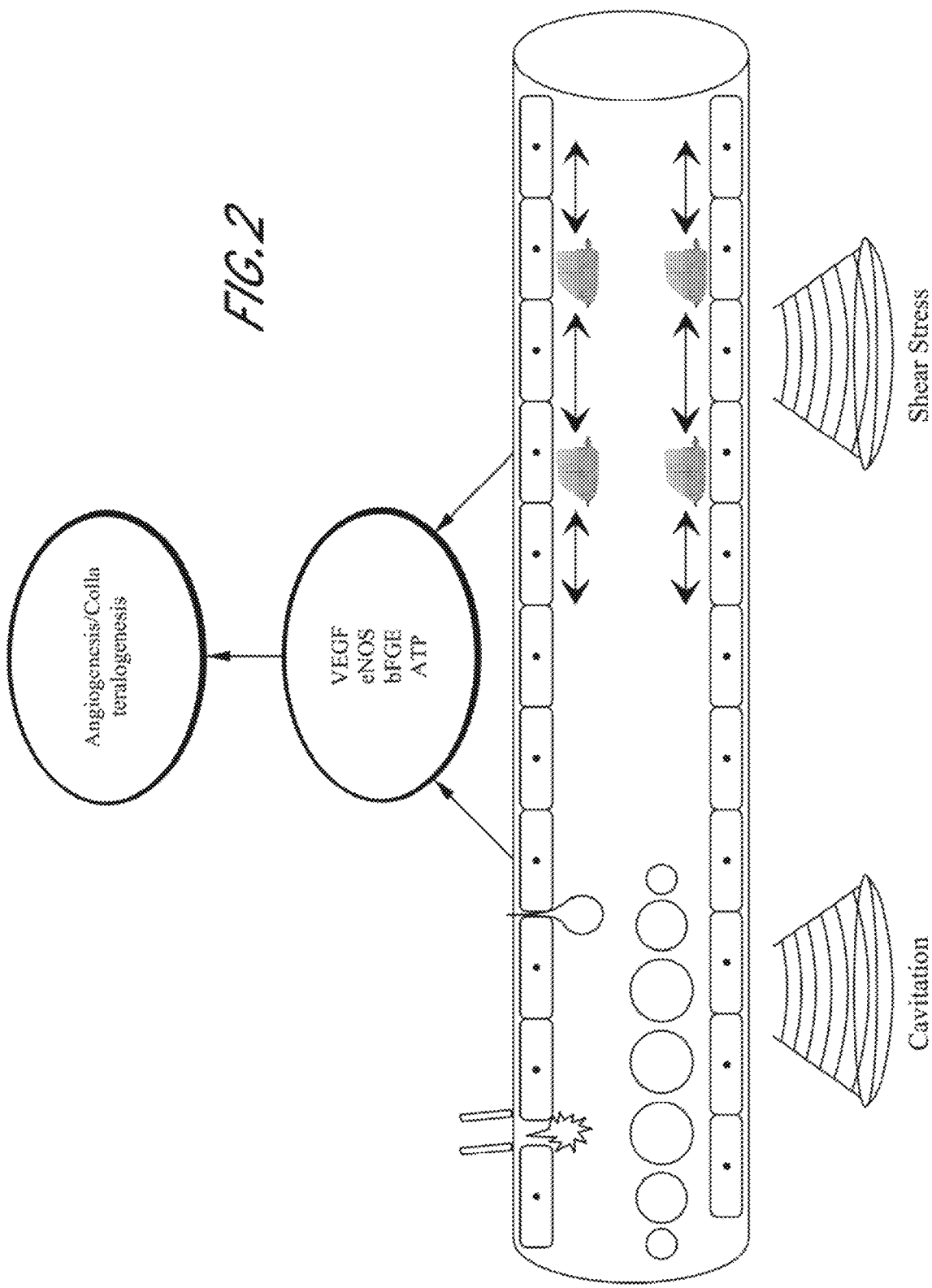

Conventional ultrasound-based treatments for both CAD and PAD have been largely limited by the fact that treatment requires a healthcare provider to be present to position and hold the device. By providing a wearable TUS sleeve that positions and fixes the ultrasound transducer or transducer array in place, treatment may be provided for up to several hours (e.g., 20 min-24 hours duration or more, including overnight therapy) at a time, thereby increasing treatment duration. Providing extended treatment duration using wearable ultrasound-based devices at predetermined parameters can in some embodiments can lead to profound and unexpected improvements in therapeutic results, including but not limited to increased blood flow from, for example, angiogenesis (forming new blood vessels). FIGS. 1 and 2 illustrates potential mechanisms of action of, for example, TUS therapy. Not to be limited by theory, such a device can be configured to increase vascular permeability from cavitation microbubbles interacting with the endothelium, and shear stresses from ultrasound waves directly onto endothelial surfaces, which can stimulate the production and/or release of growth factors, angiogenic factors and signaling molecules such as increase tissue vascular endothelial growth factor (VEGF), endothelial nitric oxide synthase (eNOS), basic fibroblast growth factor (bFGF), adenosine triphosphate (ATP), for example, leading to angiogenesis and/or collateralogenesis. Longer duration treatments can advantageously increase the local and possibly also circulating levels of these angiogenic factors among others, leading to collateralogenesis and increased microvascular density in PAD.

In contrast, some conventional systems and methods merely increase nitric oxide within tissue, thus increasing blood flow temporarily via vasodilation. However, these effects and symptomatic relief can be transient in nature and be limited to the duration of the treatment session or a short period thereafter. Not to be limited by theory, achievement of vasodilation without long-term angiogenic effects in conventional systems can be due to insufficient peak acoustic pressures and/or durations of therapy, among other reasons. As illustrated in FIGS. 1 and 2, additional mechanisms may involve acute vasodilation lasting at least 1 minute and up to 24 hours, to provide acute symptomatic relief prior to angiogenesis, such as for at least about 1, 2, 3, 4, 5, 10, 15, 20, 30, 45, 60 or more minutes, or at least about 2, 3, 4, 6, 8, 12, 16, 18, or 24 hours, or ranges incorporating any two of the aforementioned values.

Not to be limited by theory, long-term angiogenesis and collateralogenesis can occur, for example, through two or more ultrasound-mediated mechanisms, as illustrated, for example, in FIGS. 1 and 2. The first mechanism is cavitation: in some embodiments, TUS waves with sufficient peak negative pressure may cause dissolved gas to come out of solution in blood and tissue, and to convert into microbubbles. In response to TUS, these bubbles then volumetrically oscillate and/or burst, interacting with vascular endothelial cells, increasing vascular permeability, and triggering angiogenesis and collateralogenesis. While the process of cavitation is well-described, the inventors are not aware of previous techniques which specifically harness this process to promote vascular permeability and thus angiogenesis/collateralogenesis. This mechanism may also trigger up-regulation of several molecular mediators of angiogenesis/collateralogenesis as described further herein. In some embodiments, p– can be selected to promote cavitation, vascular permeability and angiogenesis/collateralogenesis without leading to harmful or lethal vascular damage.

A second mechanism is shear stress: in some embodiments, TUS waves of a desired frequency and sufficient amplitude can directly interact with endothelial cells, triggering shear stress signaling pathways, which may lead to angiogenesis and collateralogenesis. While the effects of endothelial shear stress on vasodilation and angiogenesis has been described, the inventors are not aware of previous techniques utilizing TUS to specifically increase endothelial shear stress, leading to vasodilation, collateralogenesis and angiogenesis.

TUS and SWT can in some embodiments lead to tissue-specific increases in angiogenic factors (or upregulation of receptors of growth factors) such as vascular endothelial growth factor (VEGF), e.g., VEGF-A and its receptor, FLT-1; fibroblast growth factor (FGF), e.g., bFGF the nitric oxide pathway; and stem cell differentiation. Systems and methods as disclosed herein can also potentially modulate (e.g., decrease or increase depending on the factor) levels of other factors including but not limited to VEGFR, bFGF, HIF-1-alpha, Egln1, NRP-1, Ang1, Ang2, PDGF, PDGFR, TGF-beta, endoglin, CCL2, ephrin, histamine, integrins, plasminogen activators, plasminogen activator inhibitor-1, eNOS, iNOS, COX-2, AC133, ID1/ID3, or class 3 semaphorins, among others. In some embodiments, the ultrasound-based therapy can change, such as increase or decrease circulating levels, mRNA, or other proxies of the foregoing markers by about or at least about 5%, 10%, 15%, 20%, 25%, 30%, 35%, 40%, 45%, 50%, 75%, 100%, or more after therapy compared to pre-therapy values. In some embodiments, blood flow at a desired target location can increase by about or at least about 5%, 10%, 15%, 20%, 25%, 30%, 35%, 40%, 45%, 50%, 75%, 100%, or more after therapy compared to pre-therapy values, and remain increased for about or at least about 6 hours, 12 hours, 1 day, 2 days, 3 days, 4 days, 5 days, 6 days, 1 week, 2 weeks, 1 month, 3 months, 6 months, 1 year, or even more. In some embodiments, the ultrasonic energy can be therapeutically effective to provide anti-inflammatory effects, stem cell differentiation, satellite cell differentiation, and/or modulation of prostacyclin pathways.

Endothelial cells line mature blood vessels and typically do not proliferate. However, if endothelial cells are activated by an angiogenic growth factor, they can proliferate and migrate into un-vascularized tissue to form new blood vessels. Blood vessels are surrounded by biological tissue in an extracellular matrix. The formation of new blood vessels is a function of the interactions between endothelial cells and the interaction of the endothelial cells with the extracellular matrix. These interactions are regulated by receptors on the surface of endothelial cells, which are sensitive to particular molecules such as angiogenic growth factors. Shear stress induced on endothelial cells by pressure waves can potentially reduce endothelial dysfunction and promotes angiogenesis. This effect can correlate in some cases with both with TUS amplitude ($p^-$), as well as frequency (with greater shear stress at lower frequencies). Sub-lethal microvascular permeability can result from the process of "cavitation": the formation and subsequent violent vibration/collapse of gas bubbles coming out of solution in vessels and interacting with the vessel wall via multiple mechanisms (e.g., FIGS. 1 and 2). This can be in some cases a threshold-based phenomenon, which occurs at a given p- and increases with greater intensity. In other words, angiogenesis can be caused by stress/cavitation leading to endothelial signaling, growth factor increase, and new capillary and large vessel growth.

In some embodiments, a wearable ultrasound-based device can be worn and operated for about or at least about 5, 10, 15, 20, 30, 40, 50, or 60 minutes daily, or about or at least about 2, 3, 4, 5, 6, 7, 8, 9, 10, 11, 12, 15, 18, 24, or more hours at a time (or ranges including any two of the aforementioned values), either cumulatively in multiple treatment sessions, or continuously in some cases. In some embodiments, the device can be worn and operated for between about 10 minutes and about 20 minutes; between about 20 minutes and about 40 minutes; between about 30 minutes and about 60 minutes; between about 1 hour and about 2 hours; between about 2 hours and about 4 hours; or between about 4 hours and about 8 hours per treatment session. However, in some embodiments the device is worn and operated for about, or no more than about 24, 18, 15, 12, 11, 10, 9, 8, 7, 6, 5, 4, 3, or 2 hours at a time. In some embodiments, the device can be worn and operated about or at least about once, twice, three times, or more daily; or once, twice, or three times weekly. In some embodiments, the device can be worn and operated overnight and/or while a patient is sleeping, such as between about 4 hours and about 10 hours, or between about 5 hours and about 9 hours daily or nightly, 5-7 times a week, or during the day while not sleeping.

In some embodiments, the wearable devices allow for convenient dose-response titrations to readily be performed without requiring long treatments to be performed by a medical provider using timeframes such as disclosed above.

In some embodiments, the ultrasound modality could be TUS, SWT, or a dual-mode combination thereof using one or a plurality of ultrasound transducers. In some embodiments, use of TUS (which may include HIFU, LIPUS, or other pulsed or continuous wave acoustic energies) instead of SWT can advantageously allow for titration of one, two, or more acoustic parameters to achieve a desired angiogenic effect as discussed herein. The parameters can include, for example, frequency, pulse repetition frequency (PRF), pulse duration, duty factor, and pressure amplitudes (peak positive and negative pressures; $p^+$, $p^-$). Additionally, in some cases TUS can be advantageous as it allows application of multiple sound/pressure waves in each pulse; SWT provides a single pressure wave.

Figure 3:
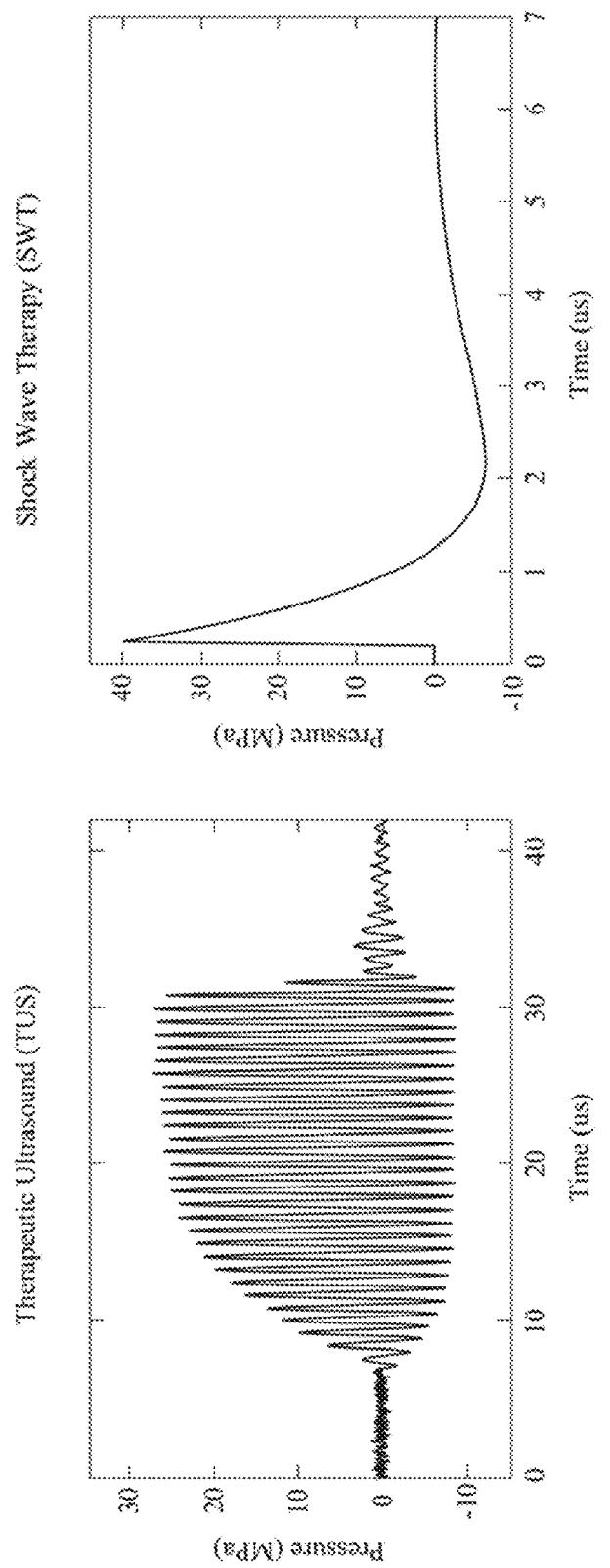
FIG. 3 illustrates sample waveforms of TUS and SWT, respectively.

Due to differences in the SWT and TUS waveforms, SWT parameters can only be adjusted to modulate pulse repetition frequency and acoustic amplitudes. FIG. 3 illustrates sample waveforms of TUS and SWT, respectively. In contrast, TUS additionally allows modulation of ultrasound frequency, pulse duration, duty factor), parameters may be titrated to improve these angiogenic effects (low frequency, high $p^-$), while avoiding acoustic intensities that may lead to thermal or cavitation-based damage. However, embodiments can also include SWT, including parameters for pulse repetition frequency and amplitudes as described herein. Furthermore, if regulatory requirements specify a maximal acoustic intensity (p, W or W/cm$^2$) to avoid cavitation-based damage, this parameter can be fixed while others can be adjusted to maximize effect. Finally, adverse effects of ultrasound are most prominent in gas-filled organs such as the lung and gastrointestinal tract in which gas unpredictably reflects and may intensify sound waves. Targeting lower extremity muscle and vasculature, which are generally free of air, can advantageously avoid these effects in some cases.

The above-described potential mechanisms of TUS-induced cavitation and shear stress can be dependent upon p- and frequency, respectively, although total dose of TUS is also determined by pulse repetition frequency (PRF), duty factor (% of time that TUS is active), and duration of therapy (time that patient wears the sleeve). Each of these TUS parameters has a toxic-therapeutic window, which can advantageously be adjusted for a desired clinical result given its wearable design and titratability of TUS parameters.

Many of the TUS mechanisms promoting angiogenesis and collateralogenesis with long-term use are also associated with acute, short-term vasodilation. Thus, certain embodiments of the device and method may be used to immediately or quickly increase perfusion for the treatment of acute limb ischemia, such as about or within about 1 minute, 5 minutes, 10 minutes, 15 minutes, 30 minutes, 60 minutes, 2 hours, 4 hours, 6 hours, 12 hours, 18 hours, or 24 hours after the onset of therapy, as well as have longer-lasting effects as disclosed herein. In some embodiments, systems and methods as disclosed herein can include only TUS and not SWT, only SWT but not TUS, or a combination of both SWT and TUS.

Frequency

In some embodiments, the frequency of ultrasound provided could be between about 250 kHz and about 3 MHz, between about 250 kHz and about 1 MHz, between about 250 kHz and about 500 kHz, between about 1 MHz and about 3 MHz, between about 750 kHz and about 1.25 MHz, between about 500 KHz and about 1 MHz, between about 2 MHz and about 3 MHz, or overlapping ranges thereof. Not to be limited by theory, lower frequencies can advantageously increase the shear stress mechanism of action. In some embodiments, lower frequencies could also penetrate more deeply into issue, although frequencies that are too low may penetrate too deeply and reach bone on the opposite end of the desired PAD field. In some embodiments, the treatment frequency could be between about 250 kHz and about 1 MHz on the thigh (deeper field from the skin of the medial thigh to the femur); between about 500 kHz and about 1.25 MHz on the calf (deep field from the skin of the posterior calf to the tibia); or between about 750 kHz and about 1.5 MHz on the ankle (shallow field from the skin of the anterior ankle to the bones), and between about 1 MHz and about 3 MHz on the plantar surface of the foot (even shallower field from skin to the tarsal and metatarsal bones), or between about 500 kHz and about 3 MHz, between about 1 MHz and about 3 MHz, and/or at least about 500 kHz or 1 MHz in any of the aforementioned locations. In some embodiments, the frequency provided can be about, more than about, or no more than about 200 KHz, 250 kHz, 300 kHz, 350 kHz, 400 kHz, 450 kHz, 500 kHz, 550 kHz, 600 kHz, 650 kHz, 700 kHz, 750 kHz, 800 kHz, 850 kHz, 900 kHz, 950 kHz, 1

MHz, 1.1 MHz, 1.2 MHz, 1.3 MHz, 1.4 MHz, 1.5 MHz, 1.6 MHz, 1.7 MHz, 1.8 MHz, 1.9 MHz, 2 MHz, 2.1 MHz, 2.2 MHz, 2.3 MHz, 2.4 MHz, 2.5 MHz, 2.6 MHz, 2.7 MHz, 2.8 MHz, 2.9 MHz, 3 MHz, 3.1 MHz, 3.2 MHz, 3.3 MHz, 3.4 MHz, 3.5 MHz, 4 MHz, 5 MHz, 10 MHz, 15 MHz, 20 MHz, 25 MHz, 30 MHz, 35 MHz, 40 MHz, 45 MHz, 50 MHz, 60 MHz, 70 MHz, 80 MHz, 90 MHz, 100 MHz, or ranges incorporating any of the foregoing values. In some embodiments, systems and methods can provide a plurality of different alternating frequencies during treatment, such as 2, 3, 4, or more different frequencies.

Pulse Repetition Frequency

In some embodiments, the pulse repetition frequency can be between about 0.1 Hz and about 100 Hz, between about 1 Hz and about 3 Hz, between about 0.1 Hz and about 1 Hz, between about 0.5 Hz and about 2 Hz, between about 1 Hz and about 5 Hz, between about 5 Hz and about 10 Hz, between about 10 Hz and about 20 Hz, between about 20 Hz and about 100 Hz, or overlapping ranges thereof. Not to be limited by theory, higher PRF can increase total delivered ultrasound energy and angiogenic effect, but may also increase transducer heating. In some cases, a very low PRF may lead to insufficient cavitation and shear stress (and only a short-term vasodilation effect), while very high PRF may lead in some cases to transducer warming, lethal vascular damage (including possible dissection, stenosis, or thromboembolism), microhemorrhage, possible nerve damage, pain, fat or other tissue necrosis, apoptosis, and/or scar formation. In some embodiments, the PRF provided can be about, more than about, or no more than about 0.1 Hz, 0.5 Hz, 1 Hz, 1.5 Hz, 2 Hz, 2.5 Hz, 3 Hz, 3.5 Hz, 4 Hz, 4.5 Hz, 5 Hz, 6 Hz, 7 Hz, 8 Hz, 9 Hz, 10 Hz 12 Hz, 14 Hz, 16 Hz, 18 Hz, 20 Hz, 25 Hz, 30 Hz, 35 Hz, 40 Hz, 45 Hz, 50 Hz, 60 Hz, 70 Hz, 80 Hz, 90 Hz, 100 Hz, 110 Hz, 120 Hz, or ranges incorporating any of the foregoing values. In some embodiments, systems and methods can provide a constant or variable PRF.

Pulse Duration

In some embodiments, the pulse duration can be between about 1 s (3 oscillations of 3 MHz) and about 100 ms, between about 1 ms and about 10 ms, between about 1 s and about 100 s, between about 100 s and about 500 s, between about 500 s and about 1 ms, between about 1 ms and about 5 ms, between about 5 ms and about 20 ms, between about 10 ms and about 50 ms, between about 25 ms and about 100 ms in some embodiments, or overlapping ranges thereof. Not to be limited by theory, longer pulses can increase total delivered ultrasonic energy and likely angiogenic effect, but may also increase transducer heating. In some cases, a very low pulse duration may lead to insufficient cavitation and shear stress (and only a short-term vasodilation effect), while very high pulse durations may lead in some cases to transducer warming, lethal vascular damage (including possible dissection, stenosis, or thromboembolism), microhemorrhage, possible nerve damage, pain, fat or other tissue necrosis, apoptosis, and/or scar formation. In some embodiments, the pulse duration provided can be about, more than about, or no more than about 1 s, 5 s, 10 s, 25 s, 50 s, 100 s, 250 s, 500 s, 750 s, 1 ms, 2 ms, 3 ms, 4 ms, 5 ms, 6 ms, 7 ms, 8 ms, 9 ms, 10 ms, 15 ms, 20 ms, 25 ms, 30 ms, 35 ms, 40 ms, 45 ms, 50 ms, 60 ms, 70 ms, 80 ms, 90 ms, 100 ms, 110 ms, 120 ms, or ranges incorporating any of the foregoing values. In some embodiments, systems and methods can provide a constant or variable pulse duration.

Duty Factor

In some embodiments, the duty factor can be between about 0.1% and about 50%, such as between about 0.5% and about 2%, between about 0.1% and about 0.5%, between about 1% and about 5%, between about 2% and about 10%, between about 5% and about 20%, between about 20% and about 50%, or about 1% in some embodiments, or overlapping ranges thereof. Higher duty factor can increase total delivered ultrasonic energy and likely angiogenic effect, but may also increase transducer heating. In some cases, a very low duty factor may lead to insufficient cavitation and shear stress (and only a short-term vasodilation effect), while very high duty factors may lead in some cases to transducer warming, lethal vascular damage (including possible dissection, stenosis, or thromboembolism), microhemorrhage, possible nerve damage, pain, fat or other tissue necrosis, apoptosis, and/or scar formation. In some embodiments, the duty factor provided can be about, more than about, or no more than about 0.05%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or ranges incorporating any of the foregoing values.

For embodiments incorporating a phased array of transducers, as demonstrated in FIG. 10, each transducer could have a duty cycle that is up to about 1/(total number of transducers), for example in an array of 8 transducers, each may have up to about a 12.5% duty cycle. Each transducer could have equal duty cycles, or unequal duty cycles in some embodiments.

Peak Negative Pressure

In some embodiments, the peak negative pressure ($p^-$; greater p– can be associated with more shear stress and cavitation, and angiogenic effect, although high p– can theoretically lead to vascular damage) can be between about 2 MPa and about 20 MPa, between about 6 MPa and about 10 MPa, between about 2 MPa and about 4 MPa, between about 1.5 MPa and about 4 MPa, between about 1 MPa and about 4 MPa, between about 2.5 MPa and about 3.5 MPa, between about 3 MPa and about 5 MPa, between about 4 MPa and about 6 MPa, between about 5 MPa and about 7 MPa, between about 7 MPa and about 10 MPa or less than about 4 MPa in some embodiments. For clarity, the minus signs preceding the peak negative pressure disclosed herein are omitted—for example, a peak negative pressure of 4 MPa (can be denoted elsewhere as −4 MPa) as described herein is more negative than a peak negative pressure of 1 MPa (can be denoted elsewhere as −1 MPa). In some embodiments, the $p^-$ may be selected to maximize sub-lethal cavitation. In some cases, a very low $p^-$ may lead to insufficient cavitation and shear stress, while very high $p^-$ may lead in some cases to transducer warming, lethal vascular damage (including possible dissection, stenosis, or thromboembolism), microhemorrhage, possible nerve damage, pain, fat or other tissue necrosis, apoptosis, and/or scar formation. In some embodiments, the $p^-$ provided can be about, more than about, or no more than about 0.5 MPa, 1 MPa, 1.5 MPa, 2 MPa, 2.5 MPa, 3 MPa, 3.5 MPa, 4 MPa, 4.5 MPa, 5 MPa, 5.5 MPa, 6 MPa, 6.5 MPa, 7 MPa, 7.5 MPa, 8 MPa, 8.5 MPa, 9 MPa, 9.5 MPa, 10 MPa, 10.5 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 25 MPa, or ranges incorporating any of the foregoing values.

Acoustic Intensity

In some embodiments, the ultrasound parameters may be configured to provide an acoustic dose as calculated at the surface, or the target tissue as described herein to specifically promote angiogenesis. In some embodiments, the acoustic dose as calculated at either the surface, or by derated $I_{spta}$ of between about 250 mW/cm² and about 5,000 mW/cm², between about 250 mW/cm² and about 720 mW/cm², between about 720 mW/cm² and about 5000 mW/cm², between about 500 mW/cm² and about 1,000 mW/cm², between about 750 mW/cm² and about 1,500 mW/cm², between about 1 W/cm² and about 2 W/cm², between about 2 W/cm² and about 4 W/cm², between about 3 W/cm² and about 5 W/cm², or overlapping ranges thereof. Derating is a method of making acoustic measurements to account for attenuation in tissue.

In some embodiments, the ultrasound parameters can be configured to provide intensity at the surface, or a derated Isppa of between about 50 W/cm² and about 1000 W/cm², such as between about 50 W/cm² and about 190 W/cm², between about 190 W/cm² and about 1000 W/cm², between about 150 W/cm² and about 300 W/cm², between about 200 W/cm² and about 500 W/cm², or between about 500 W/cm² and about 1000 W/cm², or overlapping ranges thereof. In some embodiments, the intensity at the surface, or a derated $I_{spta}$ provided can be about, more than about, or no more than about 150 mW/cm², 200 mW/cm², 250 mW/cm², 300 mW/cm², 350 mW/cm², 400 mW/cm², 450 mW/cm², 500 mW/cm², 550 mW/cm², 600 mW/cm², 650 mW/cm², 700 mW/cm², 750 mW/cm², 800 mW/cm², 850 mW/cm², 900 mW/cm², 950 mW/cm², 1,000 mW/cm², 1,250 mW/cm², 1,500 mW/cm², 1,750 mW/cm², 2,000 mW/cm², 2,250 mW/cm², 2,500 mW/cm², 2,750 mW/cm², 3,000 mW/cm², 3,250 mW/cm², 3,500 mW/cm², 3,750 mW/cm², 4,000 mW/cm², 4,250 mW/cm², 4,500 mW/cm², 4,750 mW/cm², 5,000 mW/cm², or ranges incorporating any of the foregoing values. In some embodiments, the intensity can be, for example, between about 500 mW/cm² and about 5,000 mW/cm² or between about 1,000 mW/cm² and about 4,000 mW/cm².

In some embodiments, the ultrasound parameters can be configured to provide a mechanical index (MI, defined as $MI=p^-_d/\sqrt{f}$, where $p^-_d$ is derated peak negative pressure and f is frequency) of between about 1 and about 10, such as no more than about 1.9, between about 2 and about 10, between about 1 and about 4, between about 4 and about 10, between about 1 and about 2, between about 2 and about 4, between about 3 and about 5, between about 4 and about 8, or between about 5 and about 10 in some embodiments, or overlapping ranges thereof. In some embodiments, the mechanical index provided can be about, at least about, or no more than about 0.5, 1, 2, 3, 4, 5, 6, 7, 8, 9, 10, 11, 12, or ranges incorporating any of the foregoing values.

In some embodiments, the system could be configured to deliver ultrasound energy in continuous wave (CW) mode, pulse wave (PW) mode, or both modes.

In some embodiments, the system can be configured to deliver energy with a surface intensity:vessel depth ratio to preferentially treat the target tissue (e.g., angiosome(s) in some embodiments). The surface intensity:vessel depth ratio can be, for example, about or less than about 0.75, 0.70, 0.65, 0.60, 0.55, 0.50, 0.45, 0.40, 0.35, 0.30, 0.25, 0.20, 0.15, or 0.10 W/cm³ in some embodiments, or ranges incorporating any two of the foregoing values, but in some cases at least about 0.05, 0.075, 0.10, 0.125, 0.15, 0.175, or 0.20 W/cm³.

In some embodiments, the surface intensity:vessel depth ratio is between about 0.10 W/cm³ and about 0.60 W/cm³, between about 0.10 W/cm³ and about 0.55 W/cm³, between about 0.125 W/cm³ and about 0.50 W/cm³, or between about 0.20 W/cm³ and about 0.50 W/cm³. Not to be limited by theory, such ratios among others have unexpectedly been found to advantageously treat PAD and other indications as described herein in some cases by focused ultrasound delivery to the target tissue while minimizing off-target effects.

In some embodiments, the intensity to surface area of the skin overlying the target tissue (e.g., angiosome(s)) can be about, less than about, or at least about 5:1, 4.5:1, 4:1, 3.5:1, 3:1, 2.5:1, 2:1, 1.5:1, 1:1 or less or ranges incorporating any two of the aforementioned values. Such ratios have unexpectedly been found to advantageously treat PAD and other indications as described herein in some cases.

In some embodiments, the maximum power delivered can be, in some cases, between about 30 Amps and about 70 Amps, between about 40 Amps and about 60 Amps to foot angiosomes, or about or no more than about 75, 70, 65, 60, 55, 50, 45, 40, 35, 30, 25 Amps, or ranges incorporating any two of the aforementioned values. In some embodiments, for calf angiosomes, the maximum power delivered can be, for example, between about 100 Amps and about 250 Amps, between about 125 Amps and about 225 Amps, or about or less than about 250, 245, 240, 235, 230, 225, 220, 215, 210, 205, 200, 195, 190, 185, 180, 175, 170, 165, 160, 155, 150, 145, 140, 135, 130, 125, 120, 115, 110, 105, 100 Amps, or less, or ranges incorporating any two of the aforementioned values.

In some embodiments, the surface power/intensity ratio of the ultrasonic energy delivered can be about, at least about, or no more than about 1, 2, 3, 4, 5, 6, 7, 8, 9, 10, 11, 12, 13, 14, 15, 16, 17, 18, 19, 20, 21, 22, 23, 24, or 25 cm², or ranges incorporating any two of the aforementioned values and selected to better focus ultrasound to the target tissue. In some embodiments, the surface power/intensity ratio can be, for example, between about 3 cm² and about 25 cm², between about 3 cm² and about 5 cm², between about 15 cm² and about 25 cm², or less than about 25, 20, 15, 10, 5 cm², or less.

In some embodiments, the therapeutic energy can be focused to a particular depth depending on the desired target tissue, e.g., angiosome(s). An angiosome is a 3-dimensional anatomic unit of tissue (including skin, subcutaneous tissue, fascia, muscle, and bone) fed by a source artery and drained by specific veins. The entire body can be divided into 40 angiosomes. The lower leg, below the knee and including the foot includes six angiosomes. The posterior tibial artery feeds three angiosomes (the medial calcaneal artery angiosome; the medial plantar artery angiosome; and the lateral plantar artery angiosome), the anterior tibial feeds one (the dorsalis pedis artery angiosome), and the peroneal artery feeds two (the lateral calcaneal artery angiosome and the anterior perforating branch artery angiosome). Any number of the aforementioned angiosomes can be treated to create a therapeutic effect (e.g., increased blood flow, such as via angiogenesis) using systems and methods as disclosed herein. The posterior tibial artery gives rise to a calcaneal branch, which supplies the medial ankle and lateral plantar heel, a medial branch that feeds the medial plantar instep/arch, and a lateral branch that supplies the lateral forefoot, plantar midfoot, and entire plantar forefoot. The anterior tibial artery continues on to the dorsum of the foot as the dorsalis pedis artery. The peroneal artery supplies the lateral ankle and plantar heel via the calcaneal branch and the anterior upper ankle via an anterior branch. As such, directing therapeutic energy to 1, 2, 3, 4, 5, 6, or more angiosomes, such as in the lower extremity below the knee and/or foot for example can advantageously promote angiogenesis and other benefits as described for example herein. Non-limiting examples of angiosomes to be targeted can be found in the Figures, for example, FIG. 3A, which schematically illustrates six angiosomes.

For calf angiosomes, for example, in some embodiments the energy can be focused to a vessel depth of, for example, between about 3 cm and about 9 cm, such as between about 4 cm and about 8 cm, or between about 4.5 cm and about 7 cm. In some embodiments, dorsal or plantar foot angiosomes, for example, the energy can be focused to a vessel depth of, for example, between about 1 cm and about 4 cm, such as between about 1.5 cm and about 3.5 cm, or between about 2 cm and about 3 cm. In some embodiments, the energy can be focused to a vessel depth of about, at least about, or no more than about 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, 11 cm, 12 cm, 15 cm, or ranges incorporating any two of the aforementioned values.

As some non-limiting examples, in some embodiments delivering TUS ultrasonic energy to a calf or foot angiosome(s) at a frequency of between about 1 MHz and about 3 MHz, a peak negative pressure of between about 2 MPa and about 4 MPa, energy delivery of between about 1 W/cm$^2$ and about 4 W/cm$^2$ at the target tissue level, and a surface intensity:vessel depth ratio between about 0.10 W/cm$^3$ and about 0.60 W/cm$^3$, for a cumulative total of about or at least about 10, 20, 30, 40, 50, 60, or more cumulative minutes per week for at least about 1, 2, 3, 4, 5, 6, 7, 8, 9, 10, or more weeks can surprisingly and unexpectedly promote angiogenesis and collaterogenesis in some cases.

Device Design

Conventional SWT and TUS devices have been used for CAD and are positioned in inter-costal spaces and oriented toward the area of ischemic myocardium by a trained healthcare provider. This can require at least three times a week clinical visits, which may be an undue burden on patients and the healthcare system. Similarly, SWT devices for PAD are typically too bulky to be affixed to the lower extremity with a sleeve, and also require direct positioning.

Figure 4C:
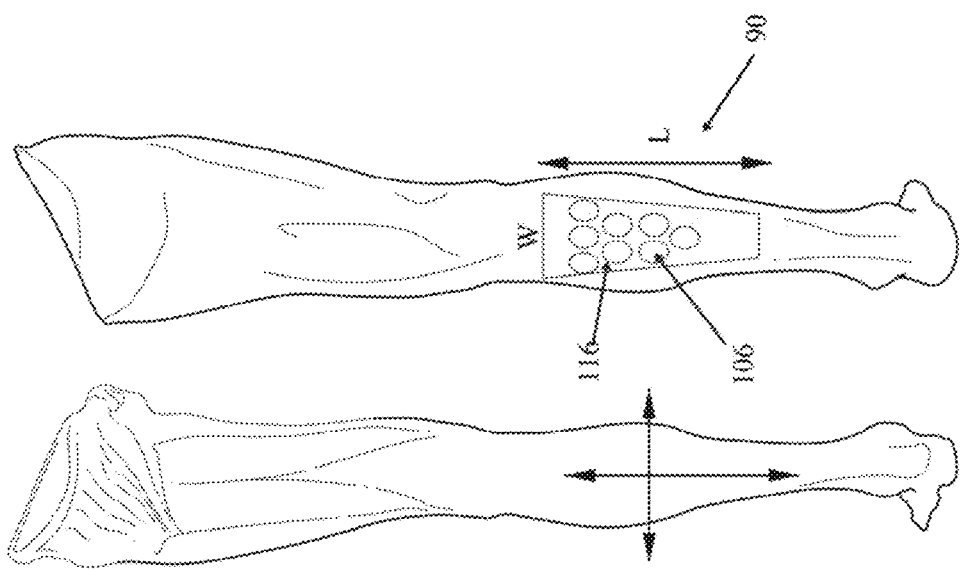
FIGS. 4A-C schematically illustrate embodiments of a wearable ultrasound-based sleeve for treating PAD, according to some embodiments of the invention.

As such, wearable ultrasound devices, such as TUS devices can advantageously allow for home-based treatment. FIG. 4A schematically illustrates an embodiment of a wearable ultrasound-based device 100 for treating PAD or another indication, according to some embodiments of the invention. The device 100 can include a wearable housing or component such as a sleeve 102 as shown, and/or a sock or other form factor. The wearable housing 102 can include a proximal end 103, distal end 107, and sidewall 105. In some embodiments, the wearable housing such as a sleeve 102 can be configured to extend completely circumferentially around a body structure as shown, or only partially circumferentially or partially around a body structure in other embodiments. The sleeve 102 could optionally include a detachable section, such as a zipper, hook-and-loop fastener material, or the like, such as axially along a length of the sleeve in some embodiments for ease in installation or removal of the device on the patient. The sleeve 102 can be elastic (or inelastic in other embodiments), and include a display and/or control 104, and a single element transducer or transducer array 106 operably attached to an inner and/or outer surface of the sleeve, and connected to a power source such as a battery, and an ultrasound generator (not shown), which can be integrated or otherwise attached to the wearable device in some embodiments. In some embodiments, the transducer or transducer array 106 can include flexible materials and generally conform to the shape of the sleeve.

In some embodiments, the device 100 can take the form of a sleeve, stocking, boot, shoe, or other form factor. After diagnosis of anatomic PAD distribution, and selection of desired treatment area in the upper or lower extremity (e.g., the thigh, calf, ankle, or foot), an initial fitting of the device 100 can be performed by the healthcare provider. Thereafter, ultrasonic treatments may take place in the patient's home without requiring the presence of a healthcare provider. In some embodiments, the transducer/array 106 can be reversibly fixed to the lower extremity treatment area with an adhesive coupling gel pack applied between the TUS transducer/array and the patient's skin. An adjustable cloth or elastic sleeve around the extremity can be designed to hold the TUS transducer and power source in place along the thigh, calf, ankle, or foot. Within a single anatomic segment (e.g., the thigh, calf, ankle), the TUS transducer and/or sleeve may be moved in an appropriate direction craniocaudally from treatment-to-treatment to target the extent of the segment requiring treatment, e.g., one, two or more specific vascular/tissue compartments (angiosomes) in deep tissue. In one embodiment, this movement could occur in an automated manner with an algorithm and motorized translation of the transducer in the sleeve, thus requiring no repositioning by the provider or patient. Movement could occur daily or weekly as desired for maximal effect. Within a single anatomic segment (e.g., thigh, calf, ankle), the TUS transducer and/or sleeve can also be rotated to target the anterior, posterior, medial, or lateral side of the extremity based on desired target. Rotation could also occur in an automated manner as described above.

Figure 4B:
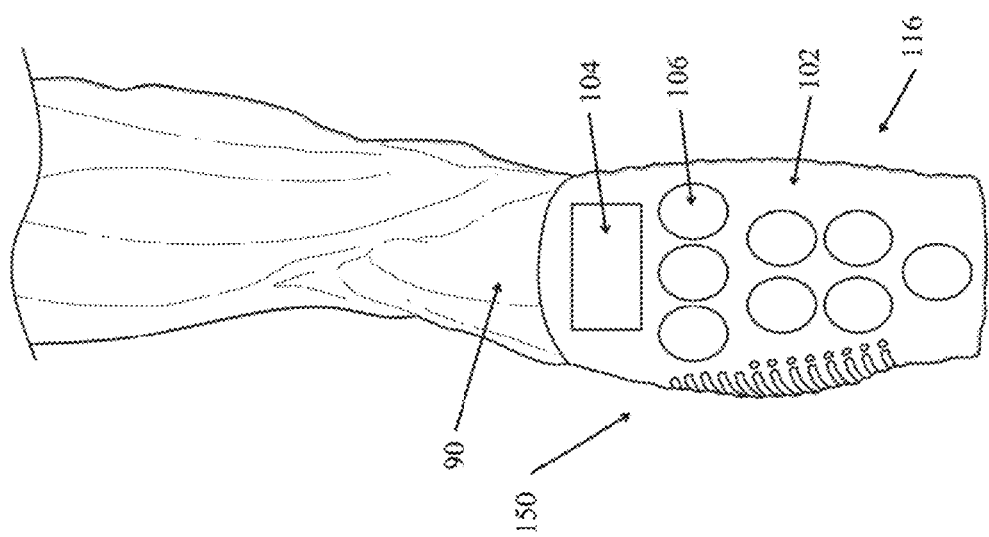
Figure 4A:
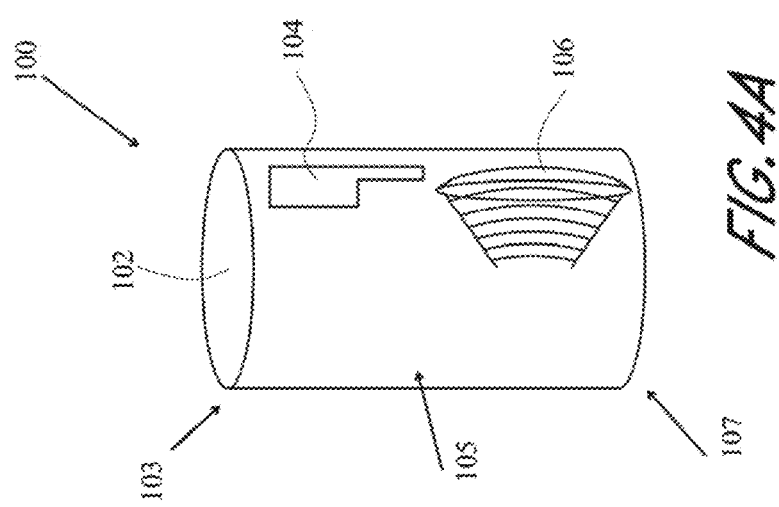

FIG. 4B demonstrates an embodiment of a device 150 with a multi-transducer array 116 including a plurality of transducers 106 (e.g., 8 transducers, or other number as indicated elsewhere herein) positioned over the posterior calf 90. FIG. 4C demonstrates schematically positioning of the transducer array 116 (some components of the device not shown for clarity) over the gastrocnemius and soleus muscles for an embodiment configured to fit around a calf 90. In some embodiments, the array 116 can have a length L of about 30 cm and a width W of about 20 cm, or other dimensions as described elsewhere herein.

Figure 4D:
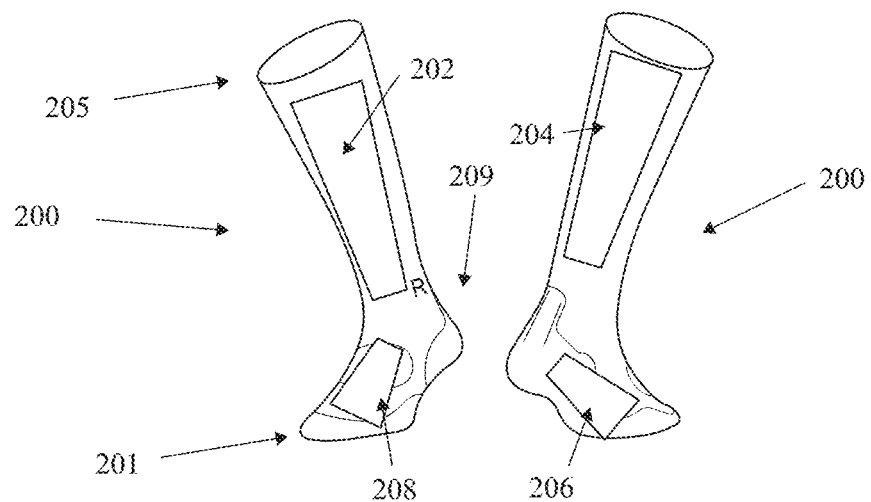
FIG. 4D illustrates a sleeve in the form of a sock that can include a closed distal end as illustrated.
Figure 4E:
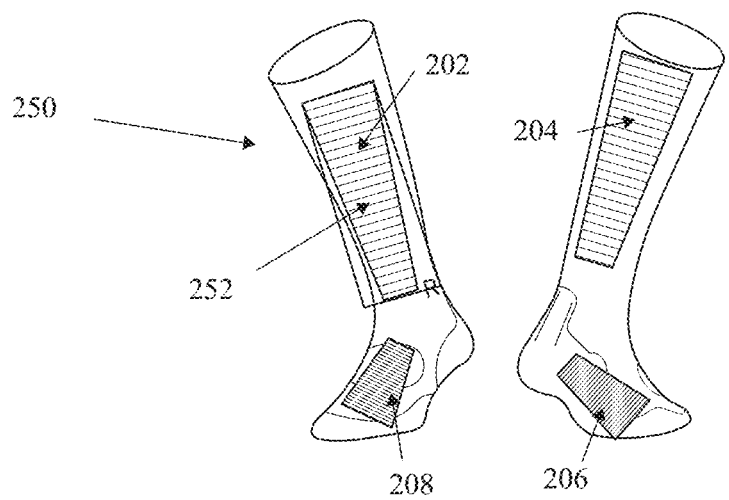
FIG. 4E illustrates an embodiment similar to FIG. 4D with different dimensions for the array.

FIG. 4D illustrates schematically anterior and posterior views of a wearable device 200 in the form of a sock that can include an open proximal end 205 and a closed (e.g. "closed toe") distal end 201 as illustrated, and be configured to curve or bend around the ankle area 209. The device 200 could have an open distal end 201 in other embodiments. The wearable device 200 can include a plurality of ultrasound transducers/arrays configured to treat the anterior tibial 202, dorsalis pedis 208, posterior tibial 204, and plantar (medial and lateral) 206 angiosomes as schematically illustrated. FIG. 4E illustrates an embodiment of a wearable device 250 similar to FIG. 4D, except that the array can be an array of transducers 252 measuring, for example, at least about 1 µm and up to about 1 cm in a dimension, such as a lateral dimension, resulting in a density of from about 1 transducer/cm$^2$ up to 1 million transducers/mm$^2$ as illustrated. In some embodiments, an array of transducers can cover about or at least about 40%, 50%, 60%, 70%, 80%, 90%, 95%, or substantially all of the outer-facing and/or inner-facing surface area of the wearable device. In some embodiments, the transducer array can circumferentially extend across about or at least about 40%, 50%, 60%, 70%, 80%, 90%, or substantially all of a transverse level of a wearable device.

Figure 4F:
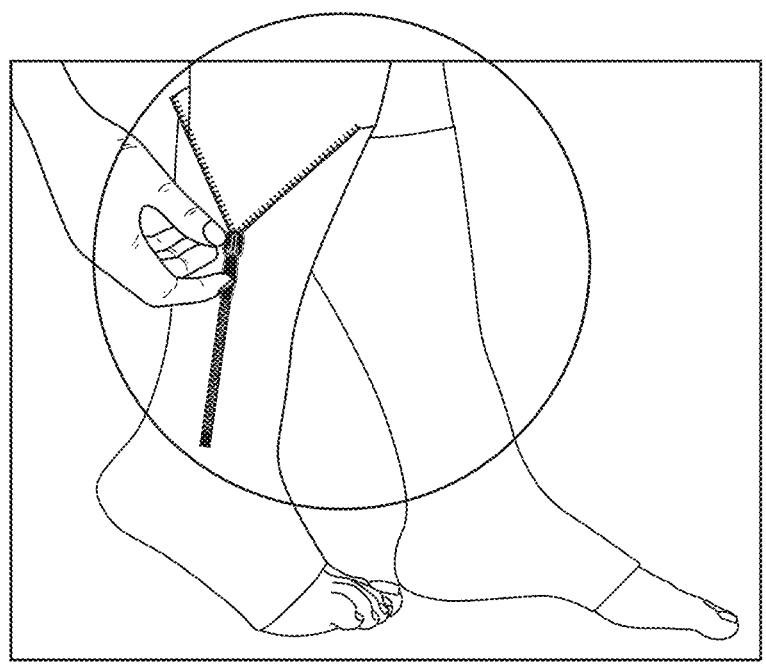
FIG. 4F schematically illustrates an embodiment of a wearable stocking with an open-toed distal end (although it can be closed-toed in other embodiments as mentioned herein).

FIG. 4F schematically illustrates an embodiment of a wearable stocking configured to conform to the lower calf and ankles with an open-toed distal end (although it can be closed-toed in other embodiments as mentioned herein). Also shown schematically is an axially-oriented zipper or similar mechanism for ease in placing or removing the device. The transducer arrays are not shown for clarity.

Figure 4G:
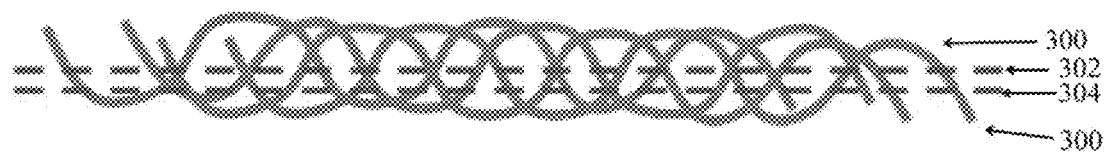
FIG. 4G illustrates a cross-section of a wearable device that includes a textile weave that can surround and/or overlap a transducer array and/or gel media layer as illustrated.

FIG. 4G illustrates schematically a cross-section of a wearable device that includes a textile weave 300 that can surround and/or overlap a transducer array 304 and/or gel media layer 302 as illustrated, such that the transducer(s) 304 can be entirely inside or circumscribed by the textile layer 300. In other embodiments, the gel 302 and transducers 304 can be sewn and adhered or otherwise attached instead of interwoven within the weave 300 as shown in FIG. 4G.

Figure 4H:
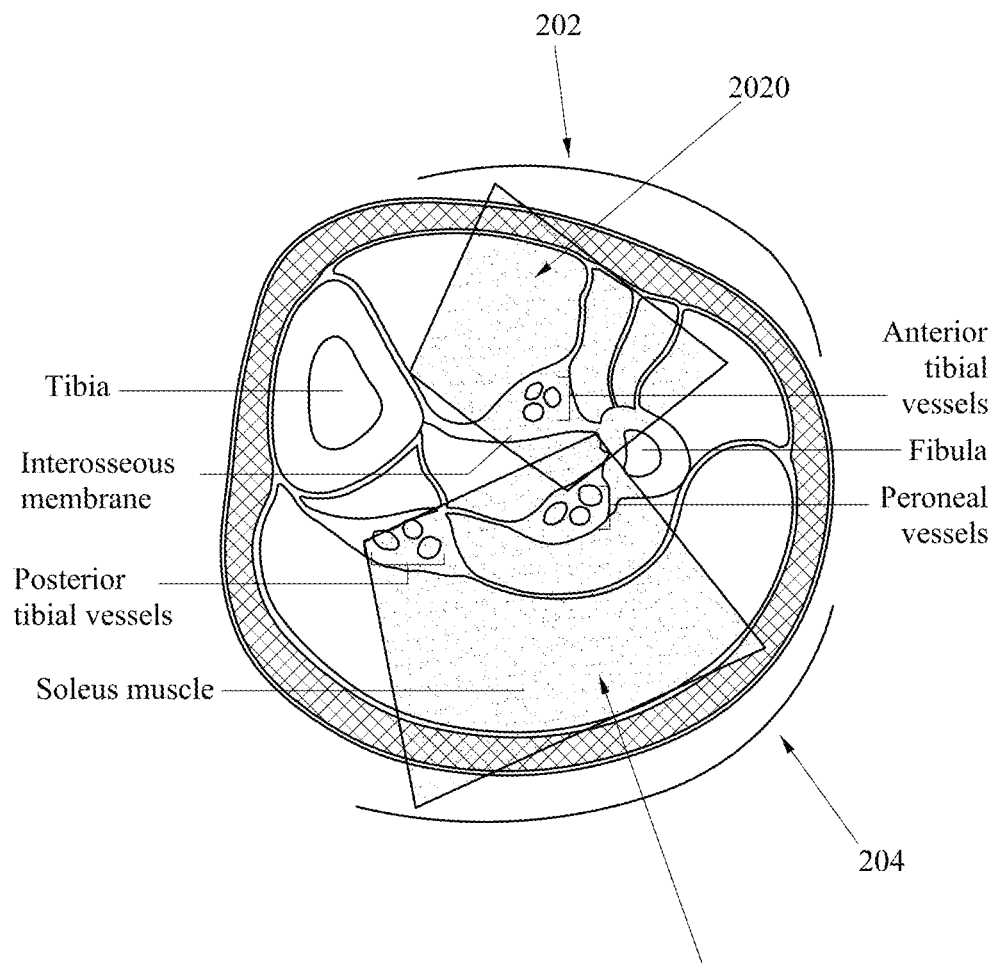
FIG. 4H illustrates a cross-section through a calf, illustrating anterior and posterior tibial vessels and surrounding structures.
Figure 41:
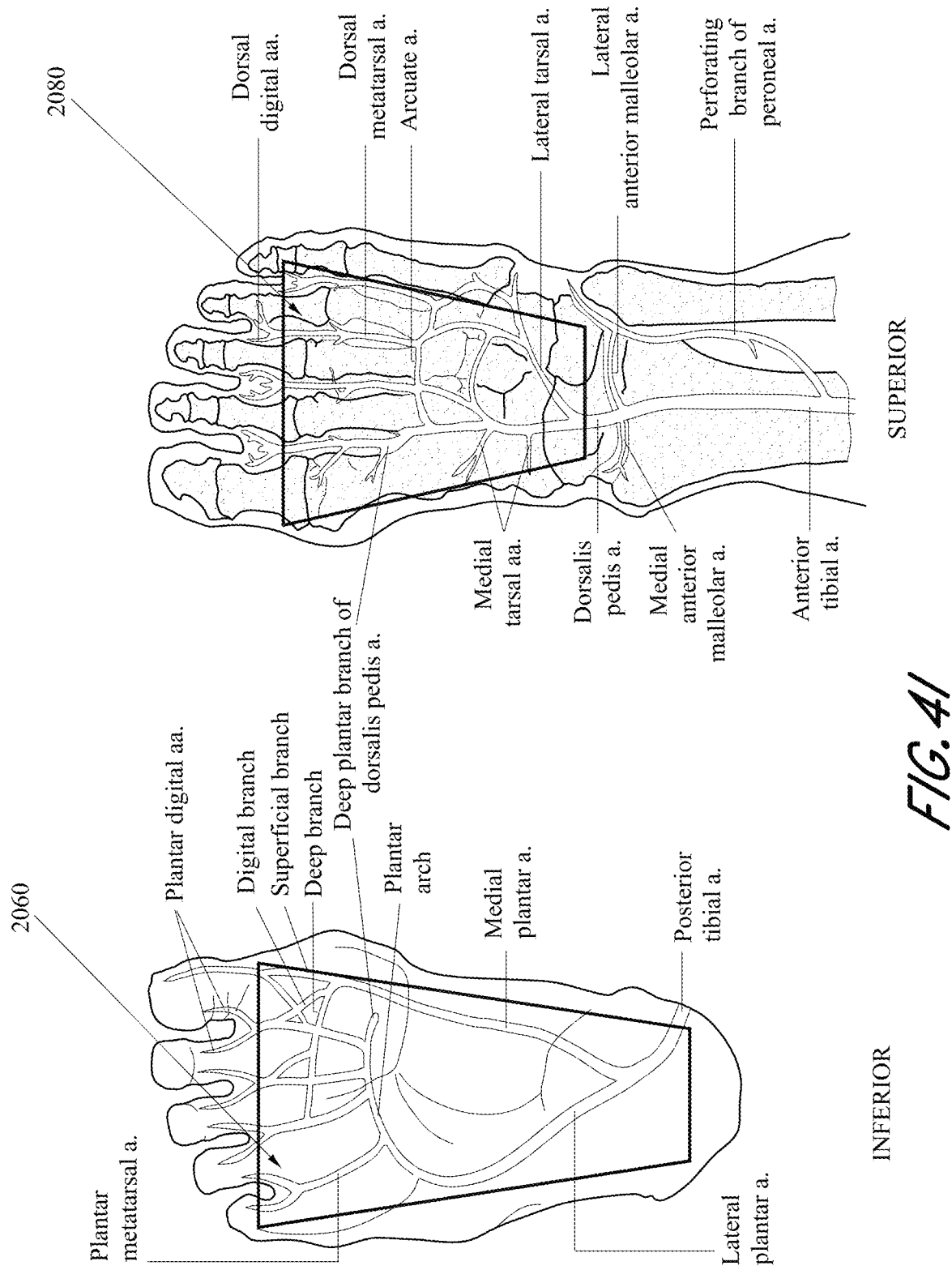

FIG. 4H illustrates a cross-section through a calf, illustrating anterior and posterior tibial vessels and surrounding structures, including the anterior tibial vessels, fibula, peroneal vessels, interosseous membrane, tibia, posterior tibial vessels, and the soleus muscle as shown. Schematic representations of a first transducer 202 placed over an anterior artery angiosome 2020 to be treated by first transducer 202 and a second transducer 204 placed over a posterior artery angiosome 2040 to be treated by second transducer 204 are illustrated (e.g., such as by embodiments described in connection with FIGS. 4D and 4E above, for example.

FIG. 4I illustrates inferior and superior views of the foot and target locations for the delivery of therapeutic energy thereto. The inferior view of the foot in the left-hand side of FIG. 4I illustrates the posterior tibial artery dividing into medial plantar artery and lateral plantar artery branches, the deep plantar branch of the dorsalis pedis artery, the plantar metatarsal artery, the plantar digital arteries, the plantar arch, and the digital, superficial, and deep branches of the medial plantar artery. The superior view of the foot in the right-hand side of FIG. 4I illustrates the anterior tibial artery, medial anterior malleolar artery, dorsalis pedis artery, medial tarsal arteries, perforating branch of the peroneal artery, the lateral anterior malleolar artery, the lateral tarsal artery, the arcuate artery, the dorsal metatarsal artery, and the dorsal digital arteries. The shaded areas schematically show parts of angiosomes 2080 (dorsalis pedis) and 2060 (medial and lateral plantar) that can be treated via energy from transducers such as 208 and 206 respectively in FIGS. 4D and 4E.

Transducers may include solid piezoelectric materials (PZT) with various backing materials (air, epoxy, and/or glass microbeads). Other embodiments may use thick or thin piezoelectric ceramic or polymer films that may be integrated using flexible transducer surfaces to allow for conformal or flexible apposition to the body. Lead zirconate titanate (PZT), lead-free piezoelectric thin films, piezopolymer films, cellulose-based electroactive paper, and other materials may be used. Films may be deposited before device fabrication, and potential advantages for application in PAD treatment include lower weight and cost, lower power requirements, wide frequency range of operation, and large amplitudes with lower driving voltages and hysteresis. In some embodiments, the device could include a piezo composite material that includes piezo ceramic materials together with passive polymers such as epoxies, or active polymers. In some embodiments, the wearable device including the transducers/transducer arrays can specifically conform and/or circumscribe the calf, ankle, and/or foot or other anatomical location of the patient.

In various embodiments, the device may contain a single-element transducer or an array of transducers. The single element transducer can be any desired shape, and in some embodiments have a focused cylindrical, focused spherical (FIG. 9), flat circular, oval, square, or rectangular shape. The transducers can in some cases have a gentle curvature (to conform to the thigh, calf or ankle). For example, a transducer configured to be placed on a thigh of a patient can have a radius of between about 10 cm and about 30 cm, and have a radius of curvature of between about 50 cm and about 300 cm. A transducer configured to be placed on a calf of a patient can be configured to have a radius of between about 5 cm and about 15 cm, and a radius of curvature of between about 25 cm and about 150 cm. A transducer configured to be placed on an ankle or plantar midfoot of a patient can have a radius of between about 2.5 cm and about 10 cm, and a radius of curvature of between about 10 cm and about 100 cm.

In some embodiments, the transducer size can be targeted to a specific target, e.g., muscle area for greater tissue coverage. The transducer or array can be conformable to the anatomical target region for more efficient and complete energy delivery. In some embodiments, a system can include a sleeve holding device to allow for longer treatment with patient motion. A power supply, such as a battery can allow for portability and enhanced patient comfort, and device placement at the bedside to allow for longer treatment.

In some embodiments, a wearable device configured to conform to the calf, e.g., a sleeve or sock can have a maximum expanded circumference (or circumference when not in use, or around a calf when in use) of between about 20 cm and about 80 cm, between about 25 cm and about 65 cm, or between about 28 cm and about 61 cm in some cases. In some embodiments, an ankle sleeve or sock (or an integrated calf-ankle sleeve or sock) can have a maximum expanded circumference (or circumference when not in use, or around an ankle when in use) of between about 10 cm and about 50 cm, between about 15 cm and about 40 cm, or between about 18 cm and about 36 cm in some cases.

The systems can include a portable, removable and/or rechargeable integrated power source and controller that can connect directly to the ultrasound transducer and also fits into the sleeve. The integrated power source and controller can allow the user and healthcare provider to specify several treatment parameters including one or more of: frequency, treatment time, duty cycle, and/or acoustic intensity. In certain embodiments, the controller can also allow the user to enter feedback regarding comfort. The controller can also record and store time and duration of treatments to allow the healthcare provider to monitor compliance. This may be done through direct connection to the controller for download of usage data, or through wireless synchronization to handheld devices or clinical remote monitoring devices. Similarly, wireless synchronization with a handheld device could allow the user to enter acoustic parameters on the handheld device to be transmitted to the battery/controller that is incorporated into the device.

The sleeve or sock could be elastic and one continuous piece, or include hook-and-loop fastener material or other reversible attachment mechanisms on one or both free ends of the sleeve, akin to a blood pressure cuff. In some embodiments, the ultrasound-based wearable device need not necessarily take the form of a circumferential sleeve; ultrasound transducers could be placed on the skin surfaces on a C-shaped sleeve that does not completely circumscribe an extremity or other body region, or discrete bandages (self-adhesive stickers, patches, or decals for example) incorporating an ultrasound transducer, for example. In some embodiments, an ankle or midfoot transducer/array may be incorporated as part of a "boot" that fits around only part of, or the entire foot, maintaining the transducer in desired anterior position and also containing the battery/ generator pack with no exposed wiring in some cases. In some embodiments, transducers or an array of transducers can deliver energy across the targeted angiosomes as described herein.

Atherosclerotic burden in PAD can be localized to larger vessels such as the iliac (common, internal or external iliac arteries), superficial femoral or popliteal arteries, medium-sized vessels such as the anterior and posterior tibial arteries, or small vessels such as those of the pedal arch. While larger vessels are often amenable to invasive revascularization with bypass surgery, angioplasty or stenting, infra-popliteal PAD is a particular challenge, as revascularization often fails. Vessels at the level of the pedal arch or below are often too small to revascularize with current methods.

Figure 8C:
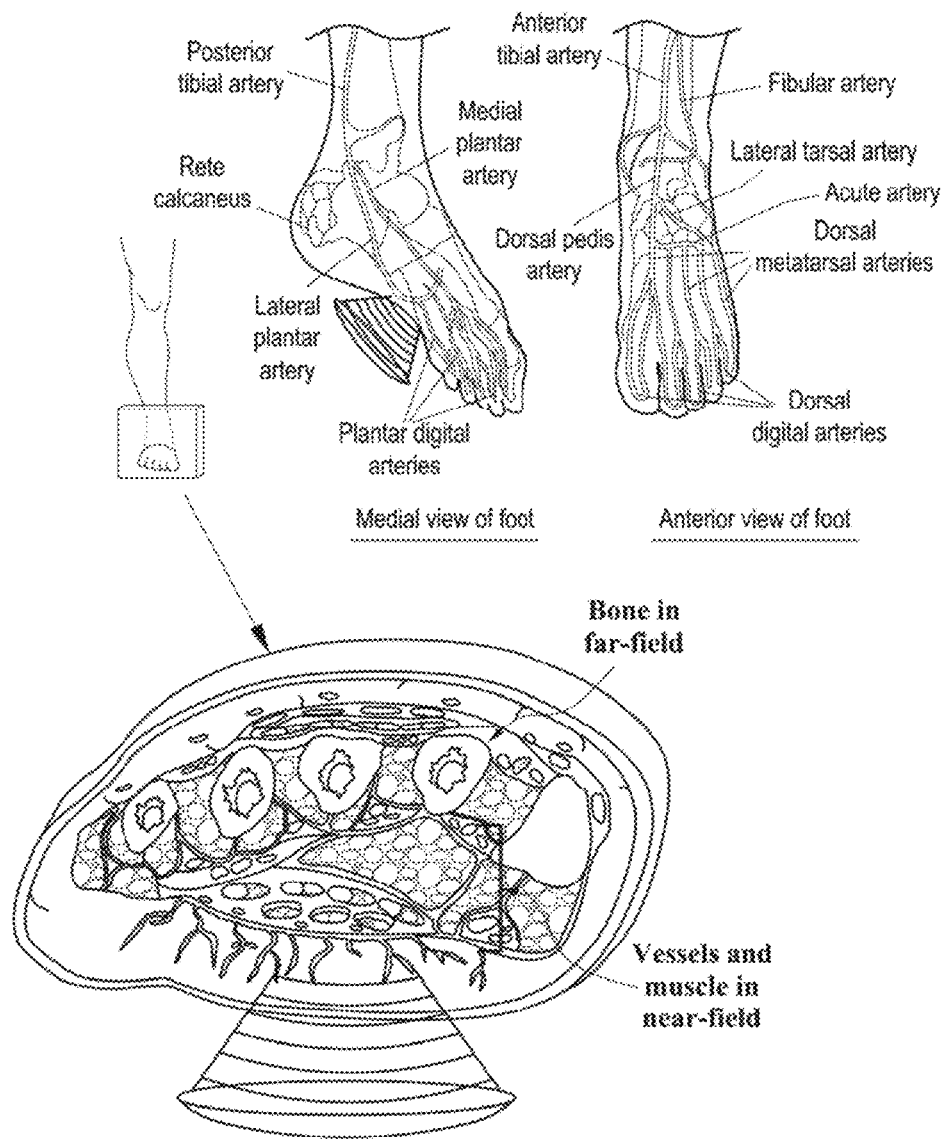

Once a diagnosis of that anatomic level of PAD is made, TUS wearable devices such as sleeves, socks, or other form factors can be chosen to focus energy on the area of interest. Not to be limited by theory, but ultrasound such as SWT and TUS can provide at least two benefits: 1) collateralogenesis: promoting collateral vessel growth around areas of macro-vascular obstruction as well as 2) angiogenesis: increasing capillary formation and microvascular density and leading to greater perfusion in distal muscle. Thus, for patients with PAD at the level of the femoral artery, a thigh sleeve may be applied to promote collateral vessel growth around stenoses, as well as a calf sleeve to increase microvascular density in the muscles of the calf. For example, patients with infra-popliteal PAD, calf and ankle sleeves may be used for collateralogenesis around the tibial arteries and pedal arch, and angiogenesis in the gastrocnemius and soleus muscle. Choice of specific sleeves/anatomic level may be left up to the clinician or prescribed via an algorithm. For example, some methods using an anatomic approach are described elsewhere herein. Suprapopliteal PAD can be treated with thigh and/or calf wearable devices such as sleeves in some embodiments (e.g., if not revascularized or previously revascularized and restenosed), while infrapopliteal PAD can be treated with calf and/or ankle or plantar foot sleeves in some embodiments (FIG. 8C). Some embodiments also provide for increased blood flow via nitric oxide-mediated mechanisms and vasodilation (which is distinct from angiogenesis).

In some embodiments, ultrasound can be delivered non-invasively to a patient sufficient to, for example, increase distal perfusion due to increased growth of collateral vessels around a macrovascular obstruction and/or increase in microvascular density (e.g., increased capillary density in a desired target location, such as the gastrocnemius).

Collateralogenesis and/or angiogenesis can potentially participate in the effect of ultrasound, such as TUS on PAD. However, depending on the distribution of PAD, TUS can be directed to specific parts of the lower extremity to harness one or both of these mechanisms.

Patients with supra-popliteal PAD can have macrovascular blockages around the vessels in the thigh, claudication in the calf due to ischemia in the gastrocnemius and soleus muscles, and may develop chronic or critical limb ischemia (CLI) due to ischemia in the digits of the foot. However, some patients have isolated infra-popliteal PAD (which can be much less amenable to revascularization), or have their supra-popliteal PAD revascularized and are left with infra-popliteal PAD. These patients have macro-vascular obstruction in the tibial arteries and pedal arch, and may also develop CLI.

Thus, ultrasound transducers may be selected and positioned particularly to target specific angiosomes including one or more lower extremity arteries and their surrounding tissues as described above. In some embodiments, use of an ultrasonic thigh sleeve around the femoral artery angiosome could promote collaterals around stenosis in the femoral artery, as well as angiogenesis in the quadriceps and/or hamstring muscles. A posterior calf angiosome sleeve could promote collaterals around the posterior tibia artery, and angiogenesis in the gastrocnemius and soleus muscles, for example. With respect to infrapopliteal disease, a calf sleeve could promote collaterals around the posterior tibia artery, while an ankle sleeve could promote collateralogenesis around stenoses in the pedal arch. FIGS. 5A-5C schematically illustrates embodiments of wearable ultrasound-based devices 500 including sleeve 102 and transducer(s) 106 for placement over the outer surface of the foot (not necessarily to scale) for treating PAD, sized and configured for placement around the thigh, calf, and midfoot respectively. In some embodiments, the sleeves and/or transducers can be configured to be movable, such as in the direction of arrows, and also showing schematically non-limiting potential stop positions.

Figure 5E:
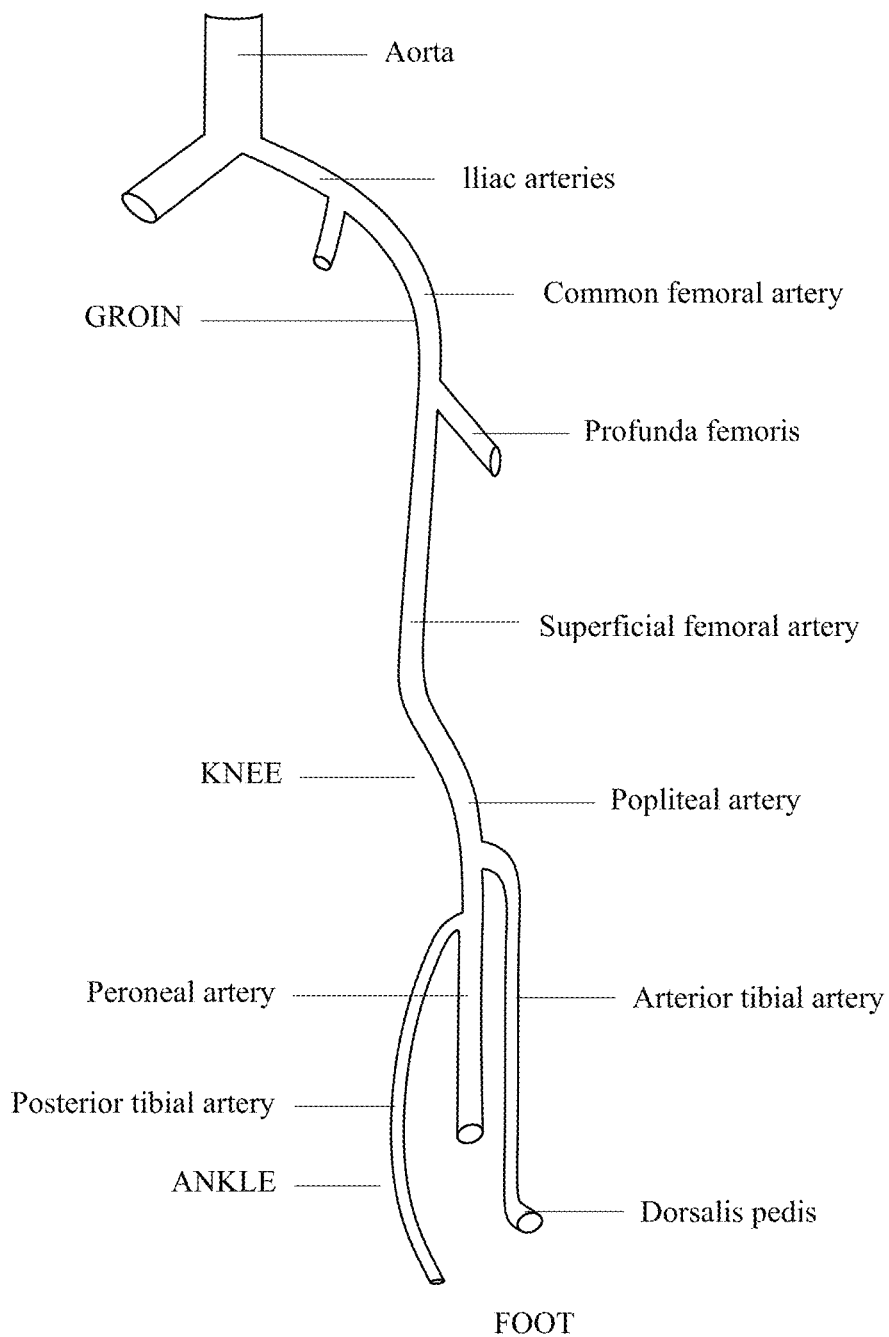
FIGS. 5A-5D schematically illustrate embodiments of wearable ultrasound-based sleeves for treating PAD, sized and configured for placement around the thigh, calf, and plantar mid-foot respectively. Also illustrated are various non-limiting arterial vessels that may be involved in PAD and treated using systems and methods disclosed herein, also in FIGS. 5E-5F.
Figure 5F:
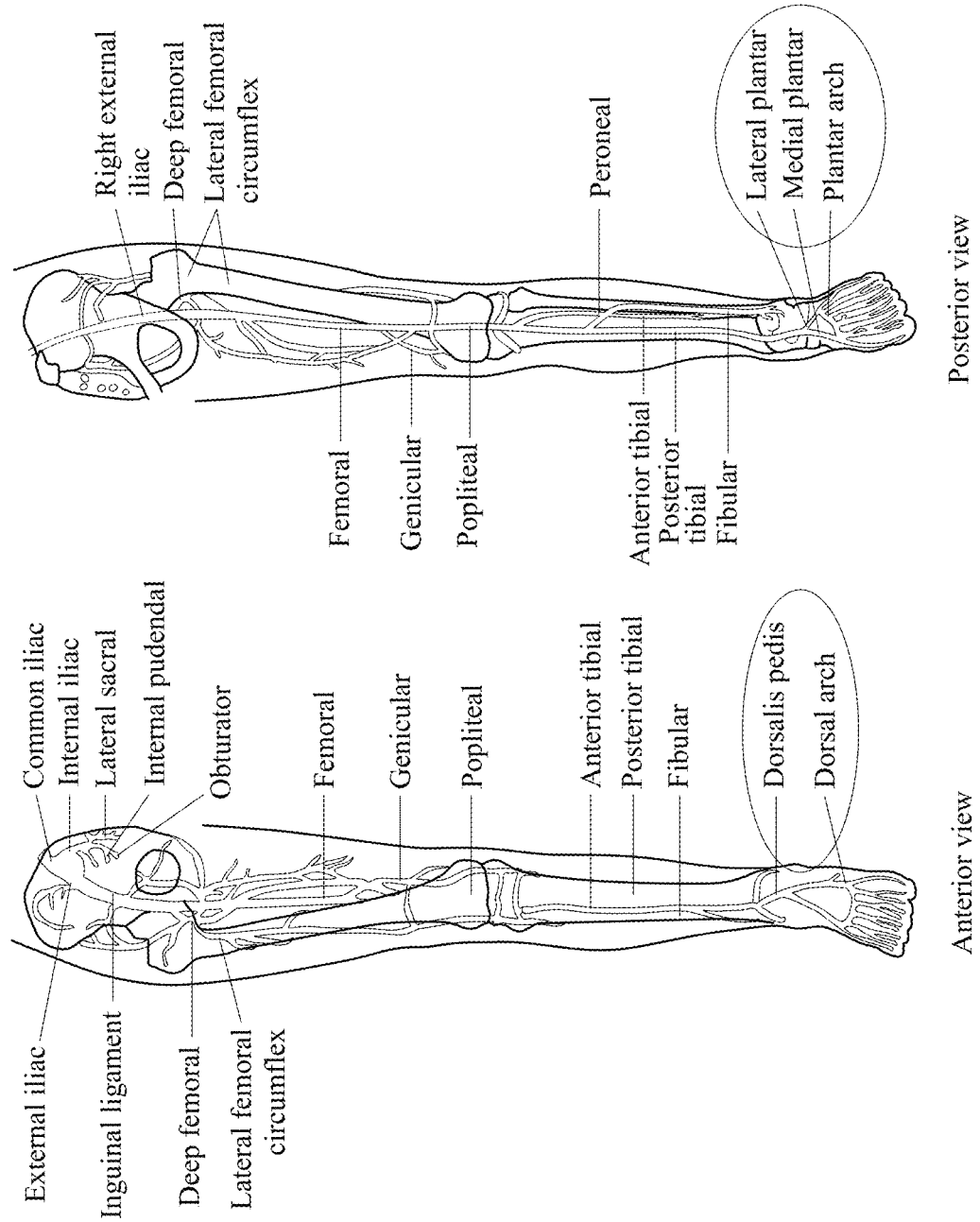

Also illustrated are various non-limiting arterial vessels that may be involved in PAD and treated using systems and methods disclosed herein (along with other anatomical landmarks) as shown in FIGS. 5D-5F, and highlighted potential vessels that can be treated in a wearable foot device, such as a sock (FIG. 5F).

In some embodiments, systems and methods can be configured for angiosome-specific positioning of the device to position major vessels and muscles in the near-field and bone in the far-field (with specific anatomic markers on the device to guide placement), e.g., about the 3 o'clock position on the medial thigh; 6 o'clock on the posterior calf, and 12 o'clock position on the plantar mid-foot wherein 12 o'clock is generally the anterior surface of the leg and foot (e.g., the patient's shin).

In some embodiments, a larger sleeve may be developed to target two or three lower extremity segments, including a separate single-element transducer or separate array for each of the two to three segments: a two-element sleeve for thigh and calf; a two-element "boot" for calf and midfoot; a three-element sleeve for thigh, calf and midfoot.

Depending on transducer size and design, the entire segment of thigh, calf, ankle, or plantar foot may not be able to be treated with the transducer in one location. Furthermore, maintaining the transducer and coupling gel or gel pack at the same skin location may predispose to infection, contact dermatitis, or simply discomfort. While the sleeve itself may be repositioned longitudinally along the lower extremity segment, to allow reliable movement of the transducer longitudinally along the sleeve. Additionally, clear numbering allows for prescription of TUS treatments by the medical provider along a given segment. In some embodiments, the ultrasonic gel or other media is self-contained within a closed pack or other housing and as such the gel or other media does not directly contact the skin surface of the patient. As such, in some embodiments, a patient advantageously may have more freedom of movement without concern that the gel or other media will spill out when the patient raises their extremity or changes position.

Figure 6B:
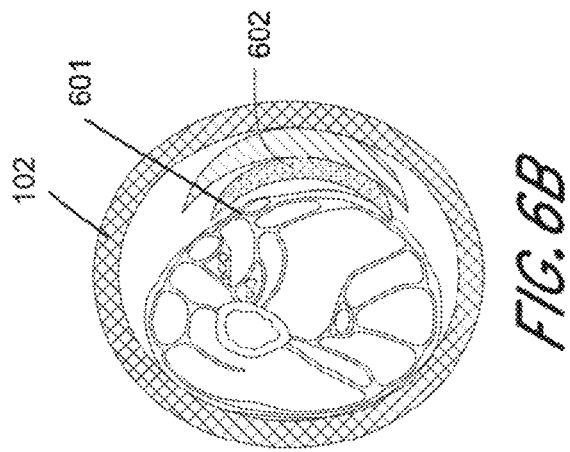
FIG. 6B illustrates an ultrasound gel pack positioned in between the ultrasound transducer and the sleeve, according to some embodiments of the invention.
Figure 6C:
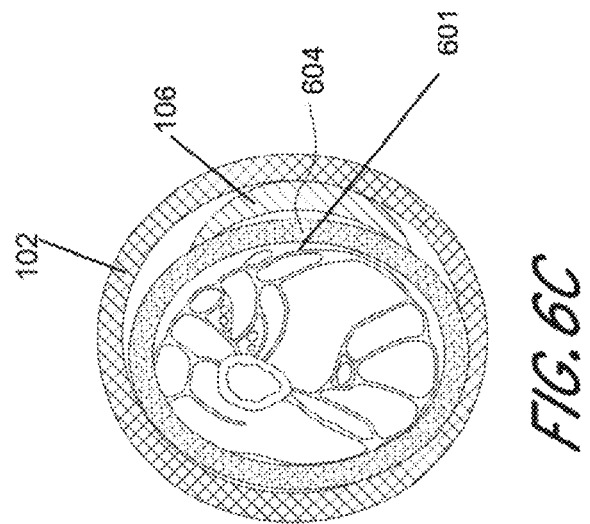
FIG. 6C demonstrates a circumferential water or gel sleeve that couples the transducer(s) to the skin.
Figure 6A:
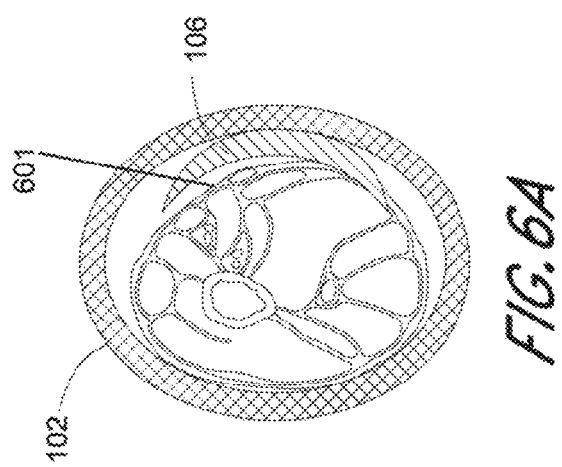
FIG. 6A illustrates a schematic cross-sectional view of wearable ultrasound-based sleeves, and a transducer positioned between the sleeve and the skin surface.

As illustrated in FIGS. 6A-6B, a coupling gel (or adhesive gel pack) can be disposed between the transducer and the skin surface. FIG. 6A illustrates a schematic cross-sectional view of a wearable ultrasound-based device including a sleeve 102, and a transducer 106 positioned between the sleeve 102 and the skin surface 601. FIG. 6B illustrates an ultrasound gel pack 602 positioned in between the ultrasound transducer 106 and the sleeve 102, according to some embodiments of the invention. The coupling gel could be, for example, a water or other media-based acoustically inert ultrasound gel manually applied to area of skin underneath the transducer. The gel could also be included in a pack (housing) filled with ultrasound gel shaped to conform to transducer surface. The pack could be, for example, adhesive on the skin side, transducer side, neither or both. The gel pack could be disposable, such as on a daily or weekly basis. Alternatively, a water-filled inner sleeve 604 positioned radially inward to the sleeve 102 and transducer 106 could be used for both coupling and cooling, as illustrated in FIG. 6C.

In some embodiments, the transducer surface can be coated with a material to prevent corrosion from frequent exposure to ultrasound gel and/or adhesive material of gel pack.

In some embodiments, the ultrasound-based device can be configured for up to three times daily or more frequency of use, elements of the device need to be disposable and/or washable to prevent infection. The sleeve can be washable (or single-use disposable in some cases), and the adhesive gel pack may be reusable or disposable as well.

FIG. 7 schematically illustrates two embodiments of the wearable ultrasound sleeve displayed in unwrapped form. In some embodiments, a wearable device, such as a sleeve can includes one or more positioning guides such as indicia, to aid the patient in appropriately positioning the transducers. In some embodiments, an "anterior" or "posterior" reference line(s) is/are drawn on the sleeve to aid patient in positioning sleeve such that transducer faces appropriate lower extremity surface. FIG. 7A schematically illustrates a wearable ultrasound sleeve 700, including an indicia of positioning, positioning guides, a transducer dock 710, and battery dock 720. For a calf sleeve for example, the indicia of positioning cranio-caudally can be located anteriorly (e.g., an axially-extending positioning line with arrows 730), while the transducer dock can be located posteriorly, although other positions are possible as described elsewhere herein. A vertically-oriented line 730 can be printed with cranial "head" and caudal "foot" orientation arrows on the sleeve or other indicia as shown in some embodiments. The patient can be instructed to orient this line with the front of the thigh (for a thigh sleeve), front of the shin/knee (for a calf sleeve), and back of the ankle (for an ankle sleeve), for example. The transducer docks can be positioned at an appropriate distance from this line based on average human leg circumferences such that the transducer is aimed at the appropriate lower extremity surface or other target location. Positioning over landmarks such as the calf borders or the popliteal fossa could ensure consistent muscle and artery coverage.

In some embodiments, a longitudinal transducer "dock" is incorporated into sleeve design with several numbered locations at each site that the transducer can be secured longitudinally along the sleeve as shown in FIG. 7A. For indications such as PAD, the length of the desired treatment area within a lower extremity segment could potentially be longer than the length of a single transducer. Furthermore, maintaining the transducer and coupling gel or gel pack at the same skin location may predispose to infection, contact dermatitis, or simply discomfort. For example, the gastrocnemius/soleus and length of posterior tibial artery may be longer than a transducer within a calf sleeve; or the length of femoral artery to be treated for a thigh sleeve. In some embodiments, a longitudinal transducer dock can allow for repositioning of an ultrasound transducer cranio-caudally along a given segment. In other words, positional guides on the transducer dock allow the patient to vary position of the single element or array of transducers between treatments while maintaining similar sleeve position. For example, the patient may be instructed to place the transducer at a first reversibly detachable dock site for a first treatment, and a second reversibly attachable dock site for a second treatment. The dock site could be, for example, a snap-fit dock, hook-and-loop fastener material, or another connector. In some embodiments, multiple ultrasound transducers can be connected to a single device, such as a sleeve and to a single power source. The transducers can be aligned axially in series, circumferentially, or other configurations depending on the desired clinical result. The sleeve itself may be repositioned longitudinally along the lower extremity segment, to allow movement of the transducer longitudinally along the sleeve. Additionally, clear numbering allows for prescription of TUS treatments by the medical provider along a given segment, such as longitudinally or axially along the sleeve. In some embodiments, the device can be configured to direct ultrasonic energy to one or more of the thigh, calf, and/or foot either serially or in parallel.

FIG. 7B demonstrates an embodiment of a sleeve 700 with an 8-transducer array 707, positioning line 730, and battery/interface 720. In some embodiments for a calf sleeve for example, the positioning line 730 could be between about 20 cm and about 40 cm in length, such as about 30 cm, and the transducers could have a diameter of between about 1 cm and about 10 cm, or about 6 cm or other values as described elsewhere herein.

In some embodiments, an ankle transducer may be incorporated as part of a "boot" that fits around the entire foot, maintaining the transducer in desired anterior position and also containing the battery/generator pack with no exposed wiring. Similarly a foot transducer may be incorporated as part of a "sock" that fits around the foot and with transducers facing the plantar foot surface. In some embodiments, the sock could be closed or open toes, that is have either closed or open distal ends depending on the desired clinical result.

SWT, by definition, provides only one pressure wave in each pulse, limiting the negative pressure pulses that may lead to angiogenesis via cavitation or shear stress. TUS provides multiple pressure waves in each pulse, potentially allowing for more frequent delivery of negative pressure pulses, as illustrated schematically in FIG. 3 discussed above. TUS may increase tissue VEGF levels compared with SWT and sham therapy. TUS and SWT can also increase gastrocnemius microvascular density, and also improve distal perfusion. Longer TUS treatments with or without further titration of TUS parameters can further increase these synergistic effects in some embodiments.

It is advantageous that the ultrasound delivered be well-tolerated by the patient. However, at certain parameters, it is possible that TUS may cause pain, discomfort, or nerve stimulation. Some TUS parameters that could result in these symptoms are $p^-$/MI and pulse duration/duty cycle, among others. In some embodiments, these parameters are controlled to stay below, such as just below the pain/nerve stimulation threshold and improve tolerance and compliance, and increase clinical effects. The parameters in some embodiments can be adjusted manually by the healthcare provider and/or the patient, such as via a user control on the device or a wired or wireless remote, such as a tablet or smartphone, for example.

Acoustic waves may be distorted by air in the interface between the transducer and the skin, reducing delivery of TUS energy to tissue, and/or resulting in transducer heating (due to reflection back to the transducer). As such, stable air-free contact between the transducer and the skin can be advantageous in some cases.

In some embodiments, the ultrasound-based wearable device includes a portable battery; connection to an external power source can be high risk in some cases and uncomfortable for nighttime use. A portable, detachable and rechargeable battery (with incorporated generator) can be connected to transducer, and also fixed into position within the sleeve. During times of non-use, the battery can be disconnected from the transducer, removed from sleeve, and connected to a charging station. Battery capacitance/voltage design can be sufficient in some cases to power a device for >8 hour use or other appropriate time period at aforementioned ultrasound parameters. However, other embodiments can include wired AC power connections.

Figure 8D:
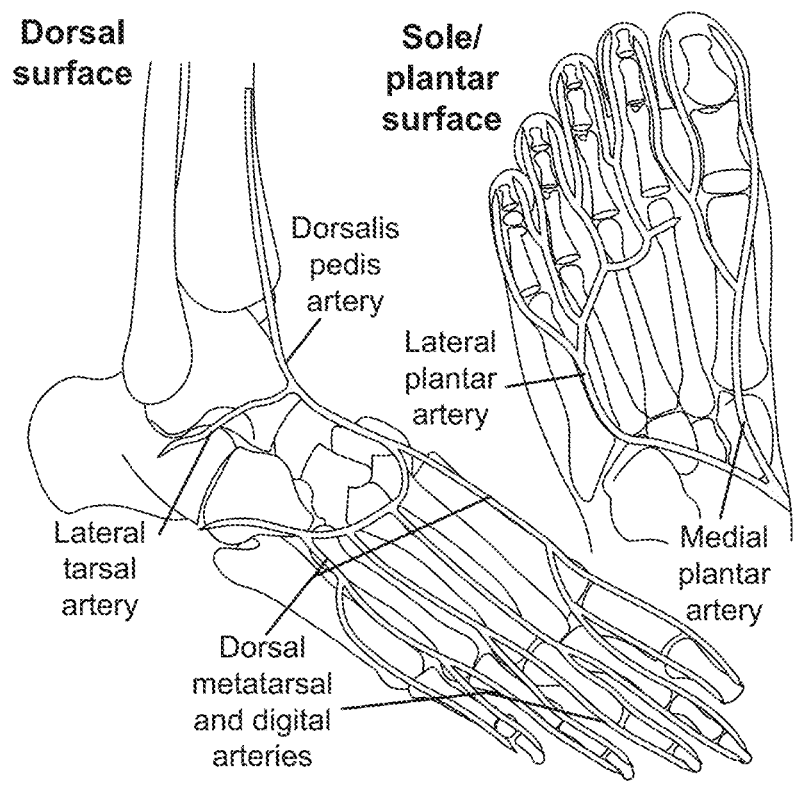

FIGS. 8A-8C illustrates non-limiting positions of an ultrasound transducer adjacent the skin surface of an anatomical target location. FIG. 8 illustrates non-limiting positions of an ultrasound transducer adjacent the skin surface of an anatomical target location. In FIG. 8A, the transducer (or array) is illustrated positioned along the medial aspect of the thigh, maintaining the femoral artery in the acoustic near-field and femur in far-field so as to maximize vascular exposure and minimize bone exposure of acoustic tissue. In FIG. 8B, the transducer (or array) is positioned over the posterior aspect of the calf, maintaining the gastrocnemius, soleus, and posterior tibial artery in the near-field, and tibia and fibula in far-field. In FIG. 8C, the transducer (or array) is positioned over the plantar mid-foot, maintaining the plantar arterial arch in the near-field and metatarsals in the far-field. Positioning of the transducers/sleeve can be determined by the health care provider depending on the desired clinical result. In the thigh, the superficial femoral artery is positioned anterior at the level of its bifurcation off of the common femoral artery, moves to the medial part of the thigh as it descends caudally, and rotates posteriorly where it becomes the popliteal artery. Thus, in some embodiments, to advantageously promote collateralogenesis around obstructions in the SFA, the transducer can be positioned along the medial aspect of the thigh. In some embodiments, the transducer can also be positioned along the anterior, posterior, or lateral aspects of the thigh. FIG. 8D schematically illustrate additional vessels on the dorsal and plantar surfaces of the foot that can be treated using systems and methods as disclosed herein.

In the calf, the popliteal artery divides to become the anterior and posterior tibial arteries. The tibia is prominently situated along the anterior portion of the infrapopliteal lower extremity, and bone reflects and distorts acoustic energy. While the transducer can be positioned anteriorly, medially, or laterally, positioning the transducer along the posterior aspect of the calf can advantageously allow for increased angiogenesis to increase microvascular density in the gastrocnemius and soleus muscles, and/or collateralogenesis around the posterior tibial artery with minimal acoustic distortion by the tibia and fibula.

In the ankle, the dorsalis pedis artery and the pedal arch run on the anterior surface of the ankle. Positioning of the transducer over the anterior surface can advantageously promote collateralogenesis around PAD in these small vessels. Furthermore, the anterior surface of the ankle is relatively flat compared to the posterior surface, allowing for more secure positioning of the transducer and gel pack. However, in some embodiments, the transducer can be positioned along the medial, lateral, or posterior surface of the ankle. The transducer can also be positioned underneath the foot to target the muscles of the feet and promote angiogenesis, such as in the sole of a shoe or shoe insert for example.

In the foot, the plantar arch continues from the posterior tibial artery and bifurcates into the lateral and medial plantar arteries. The plantar foot also include several layers of muscles, and is relatively arched in a concave shape. Positioning of the transducer on or proximate the plantar surface of the foot can simultaneously promote collateralogenesis around blockages in the plantar arch arteries and promote angiogenesis in the muscles of the feet.

Particularly with prolonged nighttime use (up to 12 hours), at higher acoustic intensities (p−, Ispta), and longer duty cycles (>10%), heating of the transducer and skin may occur. Typically, FDA requirements require a thermal index <6.0, and a probe surface not to exceed 43° C. in contact with skin, and 50° C. in air. Incomplete seal with ultrasound gel or the adhesive gel pack, resulting in significant air bubbles in the acoustic field may increase heating. Thus, safety mechanisms can be beneficial to prevent thermal skin damage. In some embodiments, a thermocouple may be integrated onto the transducer surface with a feedback loop to the battery/generator to turn off the device upon sensing a temperature greater than a predetermined threshold limit (e.g., greater than about 40° C., 41° C., 42° C., 43° C., or more or less in some embodiments). In some embodiments, the system including the transducer (or transducer array) can include a cooling system to prevent overheating and temperature control and be cooled via a fluid, such as in a closed fluid loop that circulates around the transducer, removing heat. In some embodiments, the transducer is air-cooled via one or more fans. In some embodiments, ultrasound gels with large heat capacitance can be utilized. The gels could include, for example, a conformable, high heat-capacity matrix with embedded thermal capacitors comprising phase change materials (PCMs) or other endothermic materials. In some embodiments, the thermal conductivity of the PCMs or the gel itself may be enhanced through the addition of high thermal conductivity particles. These particles can include materials such as, for example and not limitation, thermally conducting polymers, metallic nano or micro particles, carbon based materials, or other high thermal conductivity materials. In some embodiments, the sleeve can include cut-out windows, or be made of a breathable material for air cooling of the transducer. An adhesive coupling gel pack between the transducer and skin can also help to dissipate transducer heat by conduction, and limit heating of skin.

In another embodiment of the device, adequate and gasless coupling of the transducer/array to skin can be monitored by real-time, in-treatment assessment of reflected acoustic power back at the transducer. High reflected power (e.g., about or at least about 5%, 6%, 7%, 8%, 9%, 10%, 11%, 12%, 13%, 14%, 15%, or more of the forward power delivered by the generator) can be indicative of air in the transducer-skin interface, and the system can be programmed to automatically stop energy delivery in such cases.

Positioning of the sleeve and transducer/array may be varied to optimize the effects of collateralogenesis and angiogenesis by placing arteries and muscle in the acoustic near-field, and minimize acoustic reflection/scattering by maintaining bone in the far-field, as shown schematically in FIGS. 8A-8C. In one embodiment at the level of the thigh, the transducer or array could be positioned medially, maintaining the femoral artery in the acoustic near-field and femur in the far-field (FIG. 8A). In the calf embodiment, the transducer or array could be positioned posteriorly, maintaining the gastrocnemius, soleus, and posterior tibial artery in the near-field, and tibia and fibula in the far-field. In the mid-foot embodiment, the transducer/array could be positioned over the plantar surface, maintaining the plantar arterial arch in the near-field and metatarsals in the far-field (FIG. 8C).

Bone, implants (e.g., titanium implants), external braces or solid matter or other hardware, or other highly echogenic material in the near-field of the transducer can be undesirable in certain embodiments, and may lead to acoustic reflection, scattering, and may increase risk of transducer heating or other adverse events. Thus, in another embodiment, the device may include one or more ultrasound or non-ultrasound (e.g., photo or video based, such as a CCD, CMOS, or other camera configured to identify the target anatomy, X-ray, CT, or MR based) imaging components (e.g., ultrasonic sensors or software/image processing quantification of echogenicity) to assess for echogenic bone or air in the near-field. This may be incorporated into the therapy transducers themselves (A-mode imaging), or with a separate imaging transducer (M-mode or B-mode imaging). When not applying therapeutic ultrasound for example, the therapy transducers in diagnostic mode or the separate diagnostic imaging transducers can send diagnostic ultrasonic energy (e.g., in pulses) to measure reflected acoustic power. In other words, the system can include dual diagnostic imaging and therapeutic imaging functions in some embodiments. In some embodiments, the diagnostic imaging modality can be utilized to locate and identify the particular anatomy to be treated (e.g., with anatomical landmarks identifiable by the device). As such, in some embodiments systems and methods can advantageously direct and preferentially direct therapeutic energy to target tissue, e.g., the angiosomes with the energy therapy listed elsewhere herein, targeting an artery and the tissue around the artery, and minimize energy delivery to bone or other solid/relatively more echogenic tissues.

In some embodiments, the reflected acoustic energy can be sensed as a voltage from the transducer. A pre-specified upper voltage limit can be set based on known normal parameters for correct device positioning. If reflected voltage is sensed to be above this upper threshold, this will suggest echogenic bone or air in the near-field is detected, and the controller can deactivate the transducer(s) and indicate to the user that the device needs to be repositioned. In some embodiments that use an array of transducers, acoustic energy can selectively be turned off only to the transducer(s) that detect high reflected acoustic power, allowing the remainder of the array to continue providing therapeutic energy delivery. In some embodiments, bone or other undesired material can be identified by the system based on differential acoustic reflectivity, for example the system can identify bone as a predetermined, e.g., about 1.5×, 1.75×, 2×, 2.25×, 2.5×, 2.75×, 3×, or more greater than background or average, reflectivity, and energy can be directed to the near field away from the bone or other undesired material.

In some embodiments, a patient-driven method of placement can be utilized by using a "PUSH" technique-Place Until Softness Heard. As such, ultrasound intensity can be converted (such as from reflective acoustic pressure/voltage into audible sound), or other indicia. The indicia could be, for example, a visual signal (e.g., a change in brightness or color change on an LED light or display), or a quantitative score on a display; or tactile feedback such as different degrees of vibration for example, so long as the patient or provider can obtain feedback that device is positioned over soft tissues (e.g. muscle, arteries which would be quiet) rather than hard tissues (e.g. bone which would give a loud signal). In some embodiments, the signal could be binary— e.g., a warning beep or other alarm if the device is placed over hard tissues, and no sound or a confirmatory pleasant tone, etc. if the device is placed over soft tissues.

It could be useful in some cases to detect measures of blood flow and perfusion on the same platform/system that delivers the acoustic energy, or a different system. Light-based sensors that detect scattering (e.g., diffusion correlation spectroscopy or diffuse speckle contrast analysis techniques) or absorption as a function of hemoglobin concentrations in circulating blood can be incorporated. Thus, in another embodiment, a light-emitting diode and sensor can be placed in the ultrasound field, or proximal or distal to the site of ultrasound application, to determine acute (within minutes or hours) or chronic (within days or weeks) changes in perfusion as a sign of response and success of therapy. In some embodiments, angiogenesis, collateralogenesis and direct or indirect improvements in perfusion may be assessed and quantitated by perfusion-specific magnetic resonance imaging, laser Doppler imaging, angiography (including CT, MR, and intra-arterial catheter angiography, and fluorescence microangiography), systematic ulcer/wound assessment, microbubble ultrasound perfusion imaging, ankle-brachial index, toe-brachial index or transcutaneous oximetry ($TcPO_2$)"

Carotid, renal, and other arteries may be stenosed/obstructed in patients with or without PAD. In addition to the lower extremities, PAD patients often have atherosclerosis in the carotid arteries, placing them at risk for stroke and hypertension/renal injury, respectively. As with lower extremity PAD, treatment of two disease processes is typically also limited to medical therapy, and catheter-based or surgical revascularization, all of which have their limitations.

In some embodiments, an ultrasound-based device is sized and configured to fit around the neck of a patient with a transducer on a desired location, e.g., unilateral or bilateral carotid arteries. The device could take the form of a collar, for example. The device could include a circular transducer, with a spherical curvature in some embodiments. The diameter of the transducer could be, for example, between about 1 cm and about 5 cm, such as between about 1 cm and about 2 cm, between about 2 cm and about 4 cm, and or between about 3 cm and about 5 cm. The transducer could have a radius of curvature, for example, of between about 0 cm and about 50 cm. In some embodiments, the transducer could be rectangular with a cylindrical curvature. The height of the transducer could be, for example, between about 1 cm and about 5 cm, such as between about 1 cm and about 2 cm, between about 2 cm and about 4 cm, or between about 3 cm and about 5 cm. The radius of curvature of the transducer could be, for example, between about 0 cm and about 100 cm. The width of the curvature could be, for example, between about 1 cm and about 5 cm, such as between about 1 cm and about 2 cm, between about 2 cm and about 4 cm, or between about 3 cm and about 5 cm.

In some embodiments, an ultrasound-based device is sized and configured to fit around the torso, back, or abdomen with the transducer positioned over one or both renal arteries. The device could include a circular transducer, with a spherical curvature in some embodiments. The diameter of the transducer could be, for example, between about 10 cm and about 30 cm, such as between about 10 cm and about 20 cm, between about 15 cm and about 25 cm, and or between about 20 cm and about 30 cm. The transducer could have a radius of curvature, for example, of between about 0 cm and about 300 cm. In some embodiments, the transducer could be rectangular with a cylindrical curvature. The height of the transducer could be, for example, between about 10 cm and about 30 cm, such as between about 10 cm and about 20 cm, between about 15 cm and about 25 cm, or between about 20 cm and about 30 cm. The radius of curvature of the transducer could be, for example, between about 0 cm and about 300 cm. The width of the curvature could be, for example, between about 10 cm and about 20 cm, such as between about 10 cm and about 15 cm, between about 15 cm and about 20 cm, between about 12 cm and about 15 cm, or between about 15 cm and about 18 cm.

In some embodiments, the wearable device could take the form of, include, or only include, for example, a vest (for the chest), armband (for the upper extremities), glove (for the hands), boot (for the ankle), sock (for the feet), a cup or undergarment (for vascular erectile dysfunction), decal/sticker (e.g., self-adhesive), abdominal or back brace/binder (e.g., for renal or abdominal indications for example) or other form factor depending on the desired clinical result.

FIG. 9 illustrates an embodiment of a single-element transducer 900 having a circular geometry with a spherical curve (on the left), as well as a transducer 901 with a rectangular geometry with a cylindrical curve (on the right). The transducer could in some embodiments include a taper with multiple radii of curvature including first radii of curvature (a) and second radii of curvatures (b) as illustrated in the right-hand embodiment.

Unlike FIG. 9, which illustrates embodiments of spherical and cylindrically focused transducers which are concave, and thus conform to the curvature of the lower extremity, other embodiments may contain a convex transducer in which the acoustic field becomes wider than the cross-sectional area of the transducer. This may require higher power to achieve equivalent acoustic pressures at depth, but allows for treatment of a larger area of tissue with a transducer of equivalent cross-sectional area.

Other non-convex designs, for example with multiple transducers oriented at varying radial directions of focus within a flat array of transducers, may also achieve a divergent or spreading ultrasound beam for maximum muscle and vascular target coverage with minimal transducer size.

In some embodiments, the transducer can be configured to conform to the curvature of lower extremity for optimal improved and wearability. Both the transducer and battery/generator may be gently curved to conform to the curvature of the thigh, calf, or ankle. Fixed curvature transducers may be fabricated based on average human lower extremity curvatures. The curvature could be, for example, spherical or cylindrical, and have a single multiple radii of curvature along the length to best conform to anatomy. This can advantageously minimize device bulk, increase comfort, and (in the case of the transducer), limit the volume of coupling gel or gel pack and minimize risk of air incorporation into transducer/tissue interface. In some embodiments, the system can include a single device incorporating a removable/rechargeable power supply, transducer array, and sleeve can conform to thigh, calf, or foot. Alternatively, in other embodiments, one device for the entire lower extremity can treat all of the angiosomes from thigh to foot, or calf to foot.

In some embodiments, flexible piezoelectric materials may be used to allow alteration of transducer shape to fit patient's lower extremity segment. Flexible and stretchable electronic materials exist which may contain piezoelectric materials and be much thinner than conventional piezoelectric materials. Some examples of composite piezoelectric materials can take the form of pastes or paints in the form of soft or malleable materials. These materials are also referred to as piezoelectric thick film materials or piezoelectric paint. Such materials can be integrated, for example, in a band-aid design and thus adhered to the patient's anatomy.

Phased array element transducer embodiments may contain arrays of multiple transducers (e.g., 2, 4, 6, 8, 10, 12, 16, 24, 32, 64, 128, 256, 512) or more, or ranges including any two of the foregoing values) operating with one, some, or all out of phase with each other. Each element of the array may be flat circular, oval, spherical, cylindrical, rectangular, or other shapes. The surface area of each transducer element may be, in some embodiments between about 2 $cm^2$ and about 100 $cm^2$. Circular elements, for example, may have diameters between about 1 cm and about 20 cm, such as about 4 cm, about 6 cm, or about 9 cm in some embodiments. The individual array elements may be arranged within a transducer housing having non-limiting shapes (such as rhombus, oval, trapezoidal) to specifically conform to the anatomic treatment area. Each transducer in the array can be arranged such that the array is symmetric or asymmetric along one, two, or more axes. Each element of the array may be affixed to the inner surface of the sleeve with a magnetic, button-based, Velcro or glue-based mechanism. Each element can be wired to the battery/generator/interface console to allow programming for phased pulsed therapy. Embodiments with single element transducers can be fabricated with multiple different curvatures and sizes to account anatomic variations. As noted above, in some embodiments, polygons with short axes substantially parallel to the direction of curvature can be used to advantageously allow for conformability/flexibility while maintaining maximal surface area coverage, for example a diamond with the short axis oriented to the direction of curvature around the calf or foot. Array-based embodiments can allow the sleeve to more readily "wrap" around human extremities of various sizes, with the array elements conforming to the desired anatomic shape. Certain embodiments of the array-based device can allow individual array elements/transducers to be temporarily inactivated by the user or the system if they are outside the desired anatomic treatment area. The remaining elements that are placed properly over the anatomic therapeutic area can still provide the desired energy delivery.

FIGS. 10A-10F illustrates arrays of transducers in a polygonal shape, connected with a wearable component, such as a sleeve, and in some cases can include a meshwork to allow flexible coverage of a body part, for example, the calf surface from the popliteal fossa to the Achilles tendon, or for example plantar foot surface from the calcaneus to the metatarsal-phalangeal joint. Specific array shapes may be chosen to match a given patient's anatomy and the desired clinical result, as well as to optimize both desired packing densities and enhanced flexibility. Furthermore, in certain embodiments, the mesh sleeve may be made to be readily altered such that the array shape can be chosen and designed by the user to match patient anatomy. In other embodiments, polygons with short axes substantially parallel to the direction of curvature can be used to advantageously allow for conformability/flexibility while maintaining maximal surface area coverage, for example a diamond with the short axis oriented to the direction of curvature around the calf or foot.

Figure 10D:
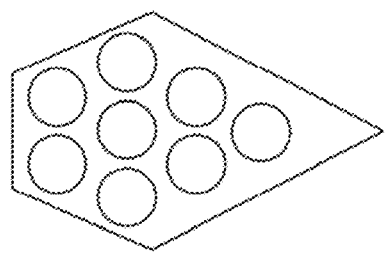
FIGS. 10A-10F illustrates arrays of transducers in a polygonal shape, connected with a wearable component, such as a sleeve.
Figure 10C:
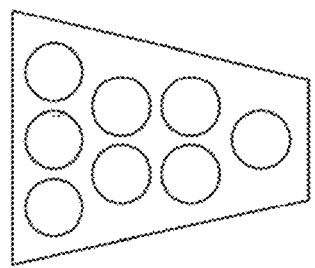
Figure 10B:
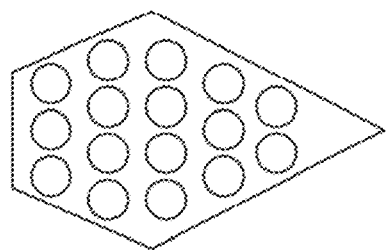
Figure 10F:
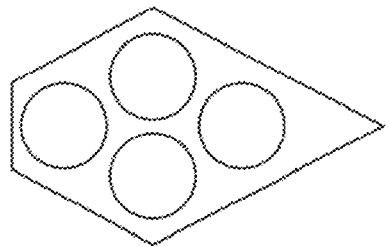
Figure 10A:
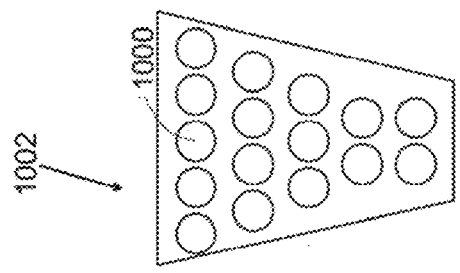
Figure 10E:
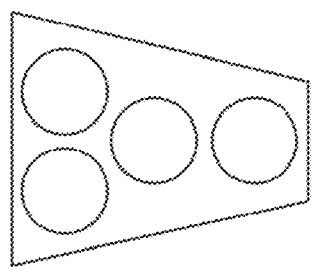

In some embodiments, each transducer could have a duty cycle that is up to 1/(total number of transducers), for example in an array of 8 transducers, each may have up to a 12.5% duty cycle. FIGS. 10A-B demonstrate two shapes of arrays 1002 of 16 circular transducers 1000 (e.g., about 4 cm in diameter in some embodiments) (FIG. 10A being a trapezoidal shape, and 10B being a diamond or truncated diamond shape). FIGS. 10C-D demonstrate two shapes of arrays of 8 circular, (e.g., about 6 cm in diameter in some embodiments) transducers (FIG. 10C being a trapezoidal shape, and FIG. 10D being a diamond or truncated diamond shape). FIGS. 10E-F demonstrate two shapes of arrays of 4 circular, (e.g., about 9 cm in diameter in some embodiments) transducers (with FIG. 10E being a trapezoidal shape and FIG. 10F being a diamond or truncated diamond shape). Other shapes are possible as noted elsewhere herein. Table 1 below compares non-limiting examples of embodiments of the surface area of each transducer and each array.

TABLE 1

| Design | # transducers | Transducer diameter (cm) | Transducer SA ($cm^2$) | Total SA ($cm^2$) |
|---|---|---|---|---|
| A | 16 | 4 | 12.56636 | 201.06176 |
| B | 16 | 4 | 12.56636 | 201.06176 |
| C | 8 | 6 | 28.27431 | 226.19448 |
| D | 8 | 6 | 28.27431 | 226.19448 |
| E | 4 | 9 | 63.6171975 | 254.46879 |
| F | 4 | 9 | 63.6171975 | 254.46879 |

Each transducer element in an array can be spaced sufficiently apart so as to avoid acoustic interaction of side lobe artifacts emanating from one transducer with adjacent transducers. The width of side lobes may be measured prior to array fabrication, and elements can thus be spaced accordingly.

In some embodiments, the adjacent transducers are driven entirely in phase. In some embodiments, adjacent transducers are driven out of phase with each other, such as about 90, 180, or 270 degrees out of phase with each other.

FIG. 11 illustrates non-limiting embodiments of a matrix of anatomic locations of transducer/array placement to optimize macrovascular collateralogenesis and microvascular angiogenesis (cross-hatched) by maintaining arteries and muscles in the acoustic near-field, and to minimize acoustic reflection (diagonal line shading) by maintaining bone in the far-field.

In some embodiments, systems and methods as disclosed herein can treat or prevent PAD, renal artery stenosis, carotid stenosis, vertebro-basilar insufficiency, brachial stenosis, axillary stenosis, or atherosclerosis or stenosis or other disease of any other vessel (including those described and/or illustrated herein) or body structure, and related vascular diseases such as atrial fibrillation or other arrhythmias, congestive heart failure (including ischemic cardiomyopathy). In some embodiments, systems and methods can be used to treat Alzheimer's or vascular dementia, and/or TIAs or ischemic stroke (e.g., with a ultrasound-based external cap or a catheter-based intravascular device for example).

The pathophysiology of diabetic foot ulcers is multifactorial, but, in part, are due to micro- and macro-vascular ischemia. Embodiments of this device may also be used for the clinical application of diabetic ulcer healing.

Other embodiments may be used to treat acute limb ischemia, hypoperfusion due to trauma and/or restless leg syndrome, which can have pathophysiologic mechanisms of vascular dysfunction and ischemia.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as ischemia. As such, treatment includes situations where the pathological condition, or at least symptoms associated therewith, are completely inhibited, e.g. prevented from happening, or stopped, e.g., terminated, such that the host no longer suffers from the pathological condition, or at least the symptoms that characterize the pathological condition. For example, treatment of PAD can result in reduction of claudication including rest-induced ischemic pain and/or exercise-induced ischemic pain, improvement in the ankle-brachial or toe-brachial index or other measurement of perfusion (including radiographic), transcutaneous oxygen pressures, duplex peak systolic velocity or velocity ratios, ankle or toe pressures, healing of ulcers, infections, or other wounds, prevention of gangrene, or other parameters. Systems and methods can also be used to treat ischemic injury as a result of trauma, battlefield injury, compartment syndrome, or even to enhance angiogenesis of tissues, organs, or even limbs after surgery or transplantation. In some embodiments, systems and methods as disclosed herein can be used to treat deep venous thrombosis (DVTs) and create venous vessel growth in the arms and legs, such as with a wearable device as described elsewhere herein. Systems and methods could also potentially be utilized to treat pulmonary embolism or pulmonary hypertension (e.g., with a thoracic vest targeting the lungs, pulmonary arteries, pulmonary veins, and/or bronchial arteries for example) to aid angiogenesis directed toward the lung vasculature, and/or offloading strain of the right heart. In some embodiments, systems and methods as disclosed herein can be utilized to treat or prevent preeclampsia or eclampsia by focusing therapeutic energy toward the placenta using parameters as described herein. Not to be limited by theory, while not well understood, preeclampsia and eclampsia can be associated with poorly developed uterine placental spiral arterioles (which decrease uteroplacental blood flow during late pregnancy), a genetic abnormality on chromosome 13, immunologic abnormalities, and placental ischemia or infarction. Diffuse or multifocal vasospasm in the placenta can result in maternal ischemia, eventually damaging multiple organs, particularly the brain, kidneys, and liver. Factors that may contribute to vasospasm include decreased prostacyclin (an endothelium-derived vasodilator), increased endothelin (an endothelium-derived vasoconstrictor), and increased soluble Flt-1 (a circulating receptor for vascular endothelial growth factor). Systems and methods (e.g., an abdominal binder, sleeve, or other wearable or other form factor) can preferentially cause promote placental angiogenesis thereby preventing or reversing the pathophysiology of placental vascular insufficiency in disorders such as pre-eclampsia and eclampsia. Treatment or prevention of ulcers may also be used for diabetic foot ulcers, with or without concomitant PAD, with similar wearable ultrasound methods and systems inducing angiogenesis. Treatment of renal artery stenosis, acute or chronic renal failure (e.g., with angiogenesis to one or both kidneys) can manifest as improved BUN, creatinine, GFR, blood pressure, plasma renin, angiotensinogen, angiotensin I, angiotensin II, ACE, or other parameters. Treatment of carotid artery stenosis can manifest as reduced transient ischemic attacks (TIA) or stroke. In some embodiments, the system can also include a diagnostic component for measuring perfusion at the anatomical location being treated, including a Doppler ultrasound perfusion measuring device or an optical perfusion measuring device, e.g., diffuse correlation spectroscopy or diffuse speckle contrast analysis in order to provide qualitative and/or quantitative measures of blood flow prior to, during, and/or after treatment sessions, which can be output to a display (in real-time in some cases). In some embodiments, the perfusion or other data can be utilized as a closed-loop feedback parameter to control or adjust therapy. In some embodiments and not to be limited by theory, Doppler or other blood flow measurements can be used to detect vasodilation using the same transducer or array, and use an acute blood flow increase above a predetermined threshold (e.g. about or at least about 5%, 10%, 15%, 20%, 25%, 30%, 35%, 40%, 45%, 50%, or more) as a proxy for ultimate angiogeneic effects. Above parameters (peak negative pressure, frequency, continuous or pulsed wave, duration, etc. can be thus customized/personalized to dial-in tailored acoustic parameters for a given patient and anatomic site, since local factors (obesity, hydration, skin thickness, etc.) can potentially affect optimal acoustics (e.g., SONAR—Sound Optimizing dilatioN for Angiogenic Response). In some embodiments, systems and methods as disclosed herein can also treat venous insufficiency (e.g., via venous collateral formation), acute or chronic pain, neuropathies, rheumatoid or osteoarthritis, cellulitis, osteomyelitis, or chronic wounds, Raynaud's or other vasospastic diseases, peripheral edema including venous stasis and lymphedema, erectile dysfunction in both males and females (e.g., via focused ultrasound to the, e.g., pudendal or clitoral artery), ischemic bowel (e.g., via focused ultrasound to arteries/tissue of the GI tract), or a variety of other indications. In some embodiments systems and methods as disclosed herein can be part of a combination therapy to achieve an unexpectedly synergistic result. In some embodiments, ultrasound systems and methods as disclosed herein could be combined with pharmacologic therapy including antiplatelet therapy such as aspirin or clopidogrel, or anticoagulation therapy such as warfarin, heparin, low-molecular weight heparin, dabigatran, rivaroxaban, apixaban, edoxaban, or other agents such as cilostazol and pentoxifylline, or thrombolytics including tPA, streptokinase, urokinase, and others. In some embodiments, systems and methods disclosed herein can treat or prevent restless legs syndrome, which may have a vascular ischemic component as noted above and thus responds to dopaminergic pharmacotherapy, which can promote vasodilation.

In some embodiments, systems and methods could include a combination of any number of the following modalities (in addition to, or as an alternative to one or more ultrasound transducers) to achieve an unexpectedly synergistic benefit: light energy (e.g., via a laser), magnetic energy such as trans-cranial magnetic stimulation, radiofrequency energy, microwave energy, mechanical energy (e.g., vibration or compression), electrical stimulation, thermal energy (e.g., warming), cooling, hypoxia or hyperoxia, or localized drug delivery. In some embodiments, systems and methods can be used to avoid an interventional procedure such as a bypass procedure, angioplasty, or stenting, or to reduce the risk of restenosis or recurrent ischemia following such procedures.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "positioning a wearable ultrasonic sleeve on a patient's lower extremity" includes "instructing the positioning of a wearable ultrasonic sleeve on a patient's lower extremity." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of treating peripheral vascular disease by stimulating vasodilation within a patient, comprising:
    providing a wearable non-invasive device comprising a flexible housing material and an array of ultrasound transducers operably attached to the flexible housing material;
    positioning the device and the array of transducers proximate a skin surface of a patient above at least one target site angiosome below the knee where vasodilation is desired, and such that the flexible housing material and the array of ultrasound transducers conforms to the skin surface of one or more of the calf, ankle, and foot of the patient; and
    causing a therapeutically effective amount of therapeutic ultrasonic energy to be directed toward the target site angiosome without delivering a drug, to stimulate cavitation and shear stress within tissue at the target site angiosome, to stimulate the production and/or release of growth factors, angiogenic factors, tissue vascular endothelial growth factor (VEGF), endothelial nitric oxide synthase (eNOS), basic fibroblast growth factor (bFGF), or adenosine triphosphate (ATP) and to stimulate vasodilation within the patient, and
    assessing acoustic or electrical parameters of individual transducers of the array of ultrasound transducers during therapy to determine the presence of bone or air in a near-field, and thereby reducing or ceasing power to one or more of the individual transducers if bone or air is found to be present in the near-field,
wherein said causing the therapeutically effective amount of therapeutic ultrasonic energy to be directed toward the target site angiosome occurs for at least 15 minutes per treatment session and for at least five treatment sessions,
wherein the therapeutic ultrasonic energy has a mechanical index in the range of 2 to 6,
wherein the therapeutic ultrasonic energy has a peak negative pressure between 1 MPa and 4 MPa,
wherein the therapeutic ultrasonic energy has a derated spatial-peak pulse-average intensity (Isppa) between 190 W/cm$^2$ and 1,000 W/cm$^2$, and
wherein each transducer of the array of ultrasound transducers is operated at a duty cycle of no more than 1%.

2. The method of claim 1, wherein the therapeutic ultrasonic energy has a frequency of between 250 kHz and 5 MHz.

3. The method of claim 1, wherein the therapeutic ultrasonic energy has a frequency of between 400 kHz and 1.5 MHz.

4. The method of claim 1, each transducer of the array of ultrasound transducers is operated at a duty cycle of no more than 0.10%.

5. The method of claim 1, wherein each transducer of the array of ultrasound transducers is operated at a duty cycle of no more than 0.05%.

6. A method of stimulating vasodilation within a patient, comprising:
providing a wearable non-invasive device comprising at least one ultrasound transducer;
positioning the at least one ultrasound transducer or an array of transducers proximate a skin surface of a patient above a target site below the skin surface where vasodilation is desired;
causing a therapeutically effective amount of therapeutic ultrasonic energy over a set time period to be directed toward the target site, thereby stimulating cavitation and shear stress within tissue at the target site, and stimulating vasodilation within the patient,
wherein the therapeutic ultrasonic energy has a mechanical index in the range of 2 to 6,
wherein the therapeutic ultrasonic energy has a peak negative pressure of between 1 MPa and 4 MPa,
wherein each transducer is operated at a duty cycle of no more than 1%, and
wherein the therapeutic ultrasonic energy has a derated spatial-peak pulse-average intensity (Isppa) between 190 W/cm$^2$ and 1,000 W/cm$^2$.

7. The method of claim 6, wherein the transducer comprises a therapeutic ultrasound (TUS) transducer.

8. The method of claim 6, wherein the wearable device is circumferentially wrapped around a portion of an extremity of the patient.

9. The method of claim 8, wherein the extremity is a lower extremity.

10. The method of claim 6, wherein the skin surface is on at least one of a thigh, a calf, an ankle, and a foot of a patient.

11. The method of claim 6, for treating peripheral vascular disease.

12. The method of claim 6, wherein positioning the at least one ultrasound transducer proximate a skin surface comprises positioning the at least one ultrasound transducer on the posterior surface of the patient's calf, the patient's ankle, or the patient's foot.

13. The method of claim 6, further comprising measuring blood flow at the target site.

14. The method of claim 6, further comprising sensing the temperature at the skin surface, and decreasing or terminating the therapeutic ultrasonic energy delivery if the temperature is above a pre-determined level.

15. The method of claim 6, further comprising assessing acoustic or electrical parameters of at least one of the individual transducers during therapy to determine the presence of bone or air in a near-field, and thereby reducing or ceasing power to the one or more of the individual transducers if bone or air is found to be present in the near-field.

16. The method of claim 15, further comprising adjusting a parameter of the therapeutic ultrasonic energy such that the target site is in a near-field, and bony structures of the patient are in a far-field.

17. The method of claim 6, wherein the target site is selected from the group consisting of: a gastrocnemius muscle, a soleus muscle, and a posterior tibial artery.

18. The method of claim 6, wherein the set time period is at least 15 minutes.

19. The method of claim 18, wherein the set time period is at least 30 minutes.

20. The method of claim 6, wherein the set time period comprises at least five treatment sessions.

21. A system for stimulating vasodilation within a patient, comprising:
a wearable non-invasive device comprising an elastic sleeve comprising at least one therapeutic ultrasound (TUS) transducer configured to be positioned proximate a skin surface of a patient above a target site below the skin surface where vasodilation is desired, wherein the ultrasound transducer is configured to cause a therapeutically effective amount of therapeutic ultrasonic energy over a set time period to be directed toward the target site, thereby stimulating cavitation and shear stress within tissue at the target site, and wherein the ultrasound transducer is further configured to stimulate vasodilation within the patient at the target site, wherein the therapeutic ultrasonic energy has a frequency of between 400 kHz and 1.5 MHz, wherein each transducer is operated at a duty cycle of no more than 1%, wherein the therapeutic ultrasonic energy has a mechanical index in the range of 2 to 6, wherein the therapeutic ultrasonic energy has a peak negative pressure of between 1 MPa and 4 MPa, and wherein the therapeutic ultrasonic energy has a derated spatial-peak pulse-average intensity (Isppa) between 190 W/cm$^2$ and 1,000 W/cm$^2$;
a portable power supply operably attached to the sleeve; and
an adhesive gel pack positionable between (a) the skin surface and (b) the at least one ultrasound transducer and the elastic sleeve.

22. The system of claim 21, wherein the at least one TUS transducer is configured to deliver the therapeutic ultrasonic energy at a pulse duration of between 1 ms and 10 ms.

23. The system of claim 21, comprising an array of TUS transducers, wherein the array of TUS transducers comprises solid piezoelectric materials and a backing material.

24. The system of claim 21, wherein the set time period is at least 15 minutes.

25. The system of claim 21, wherein the set time period is at least 30 minutes.

26. The system of claim 21, wherein the set time period comprises at least five treatment sessions.

* * * * *